United States Patent [19]

Nguyen et al.

[11] Patent Number: 4,835,263

[45] Date of Patent: May 30, 1989

[54] NOVEL COMPOUNDS CONTAINING AN OLIGONUCLEOTIDE SEQUENCE BONDED TO AN INTERCALATING AGENT, A PROCESS FOR THEIR SYNTHESIS AND THEIR USE

[75] Inventors: Thanh T. Nguyen, Tigy; Claude Helene, Saint Cyr en Val; Ulysse Asseline, La Source, all of France

[73] Assignee: Centre National De La Recherche Scientifique, Quai Anatole, France

[21] Appl. No.: 943,816

[22] Filed: Dec. 18, 1986

Related U.S. Application Data

[63] Continuation of Ser. No. 572,072, Jan. 19, 1984, abandoned.

[30] Foreign Application Priority Data

Jan. 27, 1983 [FR] France ................ 83 01223

[51] Int. Cl.[4] .................... C07H 21/02; C07H 21/04
[52] U.S. Cl. ......................... 536/27; 536/28; 536/29
[58] Field of Search .................... 536/27, 28, 29

[56] References Cited

U.S. PATENT DOCUMENTS

| | | | |
|---|---|---|---|
| 4,196,281 | 4/1980 | Heart et al. | 536/28 |
| 4,210,746 | 7/1980 | Kerr et al. | 536/27 |
| 4,321,365 | 3/1982 | Wu et al. | 536/27 |
| 4,357,421 | 11/1982 | Emtage et al. | 536/27 |
| 4,378,458 | 3/1983 | Gohlke et al. | 536/29 |
| 4,416,988 | 11/1983 | Rubin | 536/27 |
| 4,469,863 | 9/1984 | Ts'o et al. | 536/27 |
| 4,476,301 | 10/1984 | Imbach et al. | 536/28 |
| 4,500,707 | 2/1985 | Caruthers et al. | 536/27 |

FOREIGN PATENT DOCUMENTS 0063879  4/1982  European Pat. Off. .............. 536/27

OTHER PUBLICATIONS

Reuben et al., Biochemistry, vol. 17, No. 14, pp. 2915-2919 (1978).
Kubota et al., Bulletin of the Society of Japan, vol. 50(1), pp. 297-298 (1977).
Johnston et al., Science 197, pp. 906-908 (1977).
Cech et al., Biochemistry, 16, No. 24, pp. 5313-5321 (1977).
Maniatis et al., "Molecular Cloning", Cold Spring Harbor Laboratory, 1982, p. 161.

*Primary Examiner*—Johnnie R. Brown
*Assistant Examiner*—Jenny Tou
*Attorney, Agent, or Firm*—Pennie & Edmonds

[57] ABSTRACT

The present invention relates to a chemical compound which consists of an oligonucleotide or an oligodeoxynucleotide consisting of a natural or modified chain of nucleotides (sic) to which an intercalating group is fixed via a covalent bond.

7 Claims, No Drawings

NOVEL COMPOUNDS CONTAINING AN OLIGONUCLEOTIDE SEQUENCE BONDED TO AN INTERCALATING AGENT, A PROCESS FOR THEIR SYNTHESIS AND THEIR USE

This is a continuation of application Ser. No. 572,072 filed Jan. 19, 1984, now abandoned.

The present invention relates to novel chemical compounds and to their use, in particular as a probe which enables detection of a definite DNA or RNA sequence.

The chemical compounds according to the present invention consist of an oligonucleotide or an oligodeoxynucleotide containing a chain of natural or modified nucleotides, to which is attached at least one intercalated group by means of a covalent bond.

Compounds of this type which should be mentioned more particularly are the compounds of the formula:

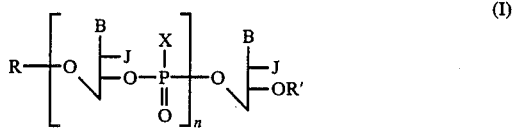
(I)

in which the radicals B can be identical or different and each represent a base of a natural or modified nucleic acid; the radicals X, which can be identical or different, each represent an oxoanion $O^\ominus$, a thioanion $S^\ominus$, an alkyl group, an alkoxy group, aryloxy, and aminoalkyl group, an aminoalkoxy group, a thioalkyl group or a grouping —Y—Z; R and R', which can be identical or different, each represent a hydrogen atom or a grouping —Y—Z; Y represents an alkylene radical in which —alk— is straight-chain or branched, a radical

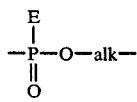

or a radical —Y"—O—Y'—, where Y" or Y' can have the meanings given for Y; E can have the same meanings as X; J represents a hydrogen atom or a hydroxyl group; Z is a radical corresponding to an intercalating agent; and n is an integer, including 0.

It is appropriate to note that the formula I represents a chain of nucleotides which can be identical or different, n simply indicating the number of nucleotides included in the molecule; n is preferably a number between 1 and 50, preferably from 1 to 25.

The intercalating agents Z are compounds which are known in techniques relating to nucleic acids, and are compounds which are capable of "intercalating themselves" in the structure of DNA or RNA.

In general, these intercalating agents consist of polycyclic compounds having a flat configuration, such as, for example, acridine, furocoumarin or ellipticine and derivatives thereof.

Of the meanings of Z, two will be used more particularly:

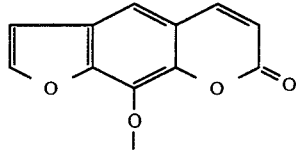
Z'

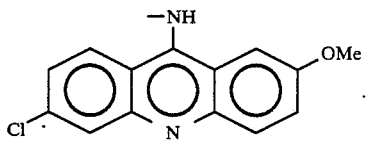
Z"

The radical B preferably consists of a natural base of a nucleic acid, for example thymine, adenine, cytosine, guanine or uracil; however, it is also possible to use bases of modified nucleic acids, in particular of halogen or azide derivatives, for example 5-bromo-uracil or 8-azido-adenine. In addition, it is possible to use photoactivatable derivatives of bases, applications of which will be seen below.

Although the radical X preferably represents an oxoanion, it can also have other meanings; if the radical X represents an alkyl grouping, this is preferably a lower $C_1$- to $C_7$-alkyl grouping, for example the ethyl, methyl or propyl groupings; if the radical X represents an alkoxy group, this is preferably a lower $C_1$- to $C_7$-alkoxy grouping, for example the methoxy or ethoxy grouping; if X represents an aminoalkyl or aminoalkoxy grouping, this can be monosubstituted or disubstituted aminoalkyl grouping or an amino radical in the form of a quaternary ammonium salt-under these conditions the substituents are preferably lower alkyl radicals as defined above; as regards the alkyl or alkoxy chain which links the amino radical to the phosphorus, this is preferably a straight-chain or branched chain containing 1 to 10 carbon atoms; finally, if the radical X is a thioalkyl radical, this is preferably a lower thioalkyl radical, that is to say containing between 1 and 7 carbon atoms.

R and R', as well as denoting hydrogen, may represent, in particular:

(a)

(b)

(c)

(d)

The radical —alk— is preferably a straight-chain or branched alkylene radical having 1 to 10 carbon atoms.

The present invention also relates to the above compounds in the form of a salt with bases or acids, and compounds in the racemic form or in the form of optically pure R or S isomers or mixtures thereof.

Examples which may be mentioned of compounds which are of more particular interest are the compounds of the formulae:

$(T-)_n(Y_1)Z_1;$ $Z_2(Y_2)(-T)_n;$ $Z_2)(-T)_n(Y_1)Z_1$ where T is the thymidine radical, n is an integer from 1 to 25 and $Y_1$ and $Y_2$ represent the $C_1$- to $C_7$-alkylene radical or a radical:

$$-(CH_2)_q-O-\underset{\underset{O}{\|}}{\overset{\overset{Me}{|}}{P}}-O-(CH_2)_p-$$

in which p and q are whole numbers from 1 to 10 and $Z_1$ and $Z_2$ have the meanings of Z, and of the formulae:

$(A-)_n(CH_2)_nZ;$ $(G-)_n(CH_2)_nZ;$ $(C-)_n(CH_2)_nZ$ and sequenced compounds, such as the oligonucleotides:

$d[A-T-A-A-A-T-T-C-A-C-(CH_2)_nZ];$ $d[A-A-T-G-G-T-A-A-A-A-T-(CH_2)_nZ].$

These compounds can be prepared by processes which are already known, in particular by the synthesis process called the "phosphotriester" process; in this process, the chain of nucleotides is first prepared, the various groupings not used being protected, and, finally, the protective groupings are removed to obtain the desired products.

In a first procedure, the compounds according to the present invention containing an intercalating grouping at 3', for example the compounds of the formula 1a, can be prepared by coupling the nucleotide of the 3'-phosphodiester of the formula 2 to the hydroxylated derivative of the intercalating agent of the formula 3 or to the 5'-hydroxylated derivative of an oligonucleotide which already possesses the intercalating agent at 3', such as 4 (equation 1).

The compounds 1b possessing intercalating groups at 5' can be obtained either by coupling of the hydroxylated derivative of the intercalating agent 3 to a 5'-phosphodiester nucleotide such as 5, or by condensation of a diester of the intercalating agent 6 with the 5'-hydroxylated nucleotide, such as 7 (equation 2).

In order to obtain compounds possessing intercalating groups both at 3' and at 5', such as 1c, it is possible, for example, to couple a diester, such as 6, to a triester of the formula 4, or, starting from a 3', 5'-bis(phosphodiester) nucleotide, such as 8, to the hydroxylated derivative of an intercalating agent 3 (equation 3).

Finally, the compounds possessing an intercalating agent linked to an internucleotidic phosphate, such as 1d, can be prepared either by coupling the hydroxylated derivative of the intercalating agent to the internucleotidic phosphodiester group 9 or by coupling a diester 2 to the 5'-hydroxylated derivative of an oligonucleotide 10 already possessing the intercalating agent (equation 4).

Dimers such as 22 and 23 and intermediate oligomers can be prepared according to one of the attached equations 5, 6 or 7; these equations relate to techniques which are already known in the so-called phosphotriester synthesis.

According to these equations, various monomers 16 and 17 and oligomers of a definite sequence can be obtained from various suitably protected nucleosides of the formula 11.

In formula 11, M represents one of the bases of natural or modified nucleic acids in which the function $NH_2$ is protected by an acyl group; JL represents a hydrogen atom or a trialkylsilyloxy grouping or another protected grouping; Tr represents a trityl grouping, a monomethoxytrityl grouping or a dimethoxytrityl grouping.

The compounds in which X is a radical of the etherified type can be prepared from suitable protected nucleosides, such as 11, using phosphorylation reagents, such as 12, 13 or 14:

The reaction conditions of these various reactions are known and are recalled in brief in the attached equations.

The dinucleoside monophosphates such as 20 and 21 in which the phosphate carries three different substituents can be obtained in the form of diastereoisomers (R or S), or in the form of the isomer 20R or 20S and 21R or 21S. The isomers 21R or 21S can be obtained either by separating the two components of the diastereoisomer or by treating each of the isomers 20R and 20S with an alcoholate.

Phosphorylation of the diastereoisomer 21R,S and of the isomers 21R and 21S with the reactants 13 and 14 leads, respectively, to dimers 22 and 23 in which the phosphate carrier of the grouping X=OR''' can be in the form of the diastereoisomer (R,S) or in one of the two isomer forms R or S.

The dimers 22 and 23 derived from phosphonic acid (X=R''') can be obtained via the metaphosphonate 24 according to equation 6.

Oligomers 2, 4, 5, 7 and 8 can be obtained from the dimers 22 and 23 (equation 7).

The preparation of an oligomer containing an internucleotidic phosphodiester group 9 is given by equation 8.

Finally, conversion of the various totally protected oligomers into compounds of the formula 1 is effected by selective elimination of the various protective groups. De-protection of the internucleotidic phosphates (dearylation) has been carried out in an anhydrous medium with the aid of the benzohydroxamate ion. According to this novel process, the arylated phosphoesters can be deblocked whilst at the same time preserving the alkylated phosphoester and the intercalating groupings used.

Finally, the compounds according to the invention can be prepared by semi-synthetic methods, in particular using DNA or RNA fragments which are prepared by genetic engineering methods and to which the intercalating agents are subsequently attached.

EQUATION 1

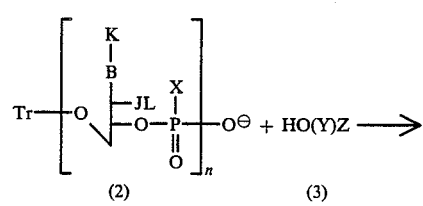

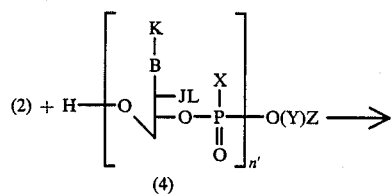

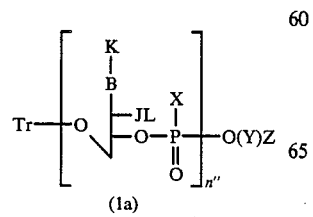

EQUATION 2

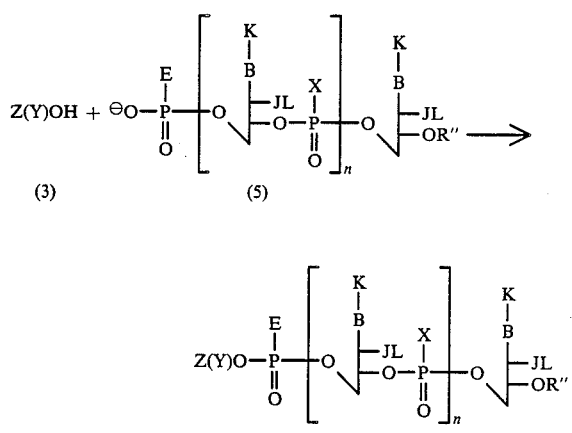

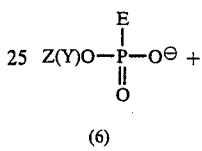

EQUATION 3

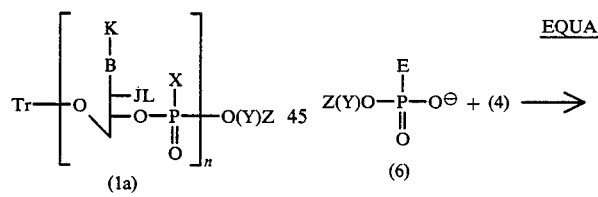

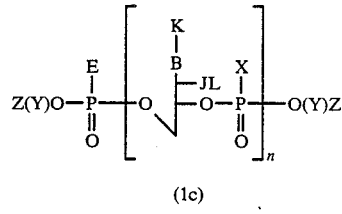

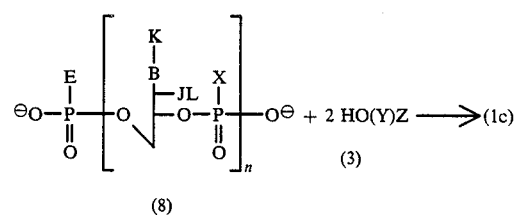

EQUATION 4
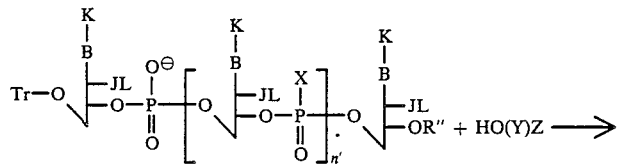
(9)
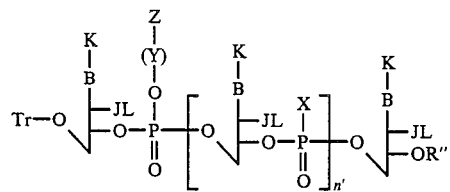
(1d)
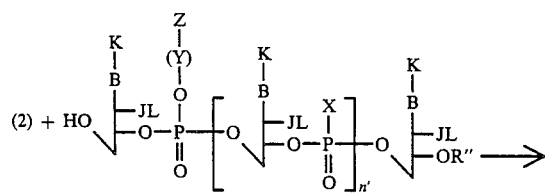
(10)
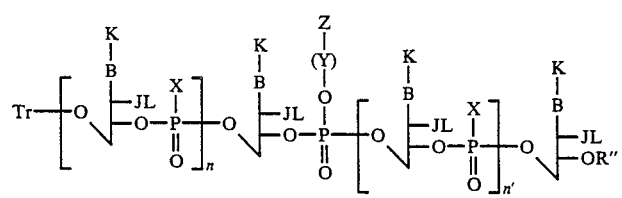
(1d)
EQUATION 5

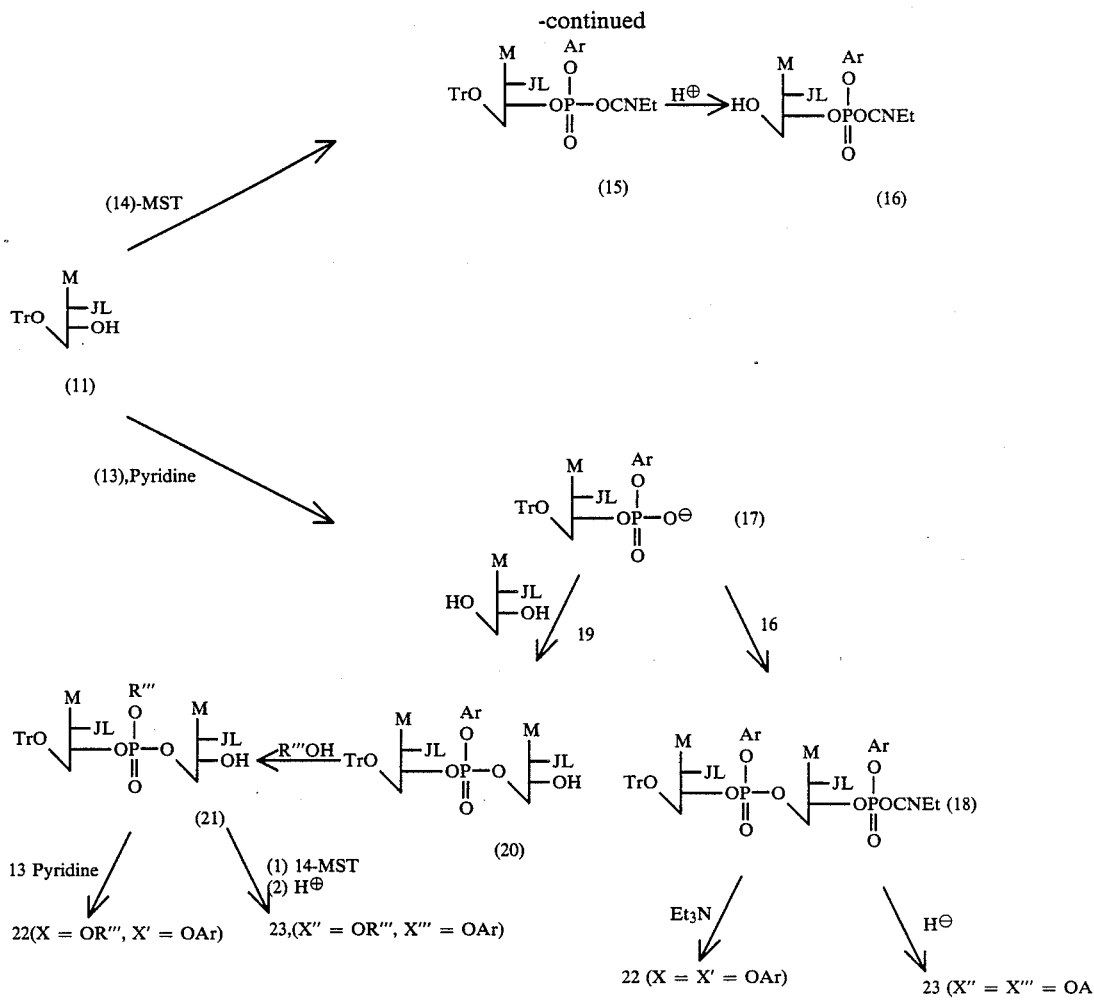
EQUATION 6
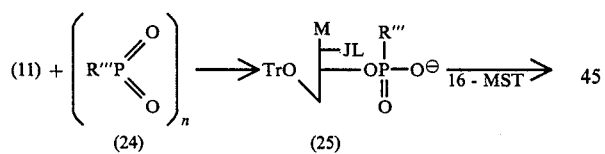
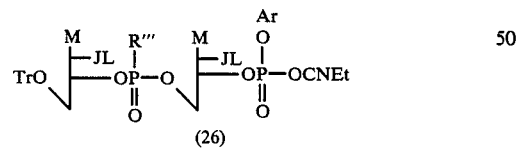
EQUATION 7
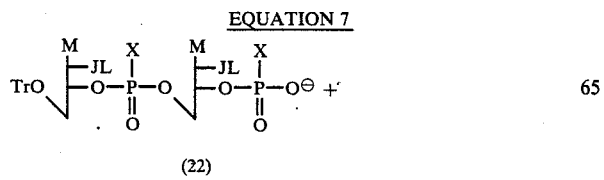
-continued
EQUATION 7
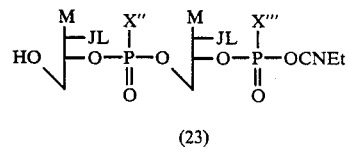
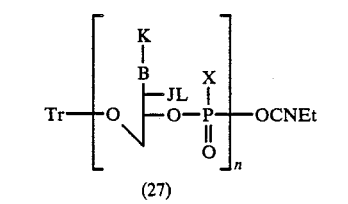

-continued
EQUATION 7

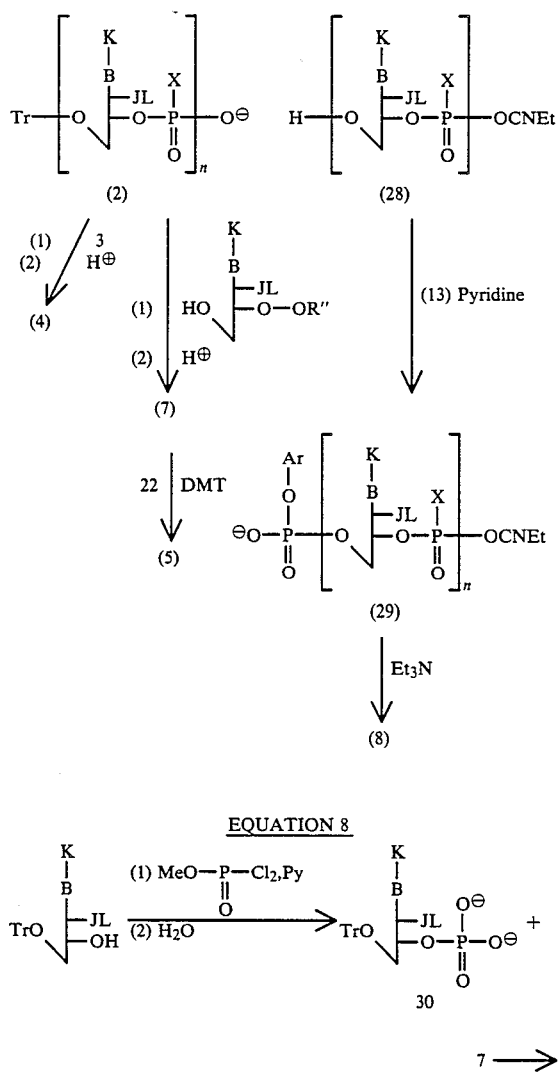

EQUATION 8

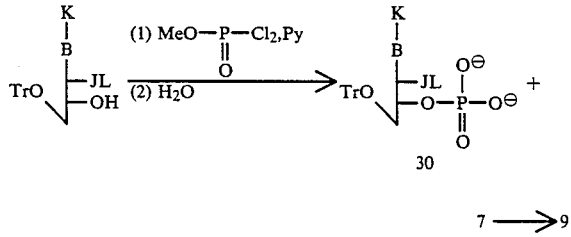

$7 \longrightarrow 9$

The compounds according to the present invention consisting of a chain of oligonucleotides and an intercalating agent bond selectively to any complementary sequence of oligonucleotides. The presence of an intercalating agent in the compounds according to the invention enables the affinity of the compound for the complementary oligonucleotide to be improved with respect to the oligonucleotide by itself.

The presence of intercalating agents which have properties distinct from those of the nucleotides permits their detection and thus detection of the presence of a chain of nucleotides complementary to the chain of which they form part.

The compounds according to the present invention can thus be used as a hybridization probe, but also as a purification component for definite DNA or RNA sequences.

The presence of intercalating agents thus permits in situ detection of attached compounds, for example by fluorescence before photochemical bridging, in the case of acridine derivatives, or after photochemical bridging, in the case of furocoumarin derivatives.

This means that the compounds according to the present invention can be used to detect a given sequence in a DNA or RNA fragment, for example by hybridization on gel.

The compounds can also be used to detect mutations at the DNA or RNA level. If a base (for example G) in a normal gene has been replaced by another base (for example T) in the gene subjected to mutation, it is possible to construct an oligodeoxynucleotide which terminates at the side of 3' by A, the intercalating group being attached to the phosphate grouping at 3'. The pairing will be complete with the mutated gene, while the last base pair with the normal gene will not be able to form. This will involve a disturbance in the interaction of the intercalating agent, which will amplify, from the point of view of the stability of the complex formed, the absence of pairing. The same effect can be obtained by choosing the mis-paired base at the side 5' of the oligodeoxynucleotide, the intercalating grouping being bonded to the phosphate group at 5'.

For example, the two oligodeoxynucleotides $(Tp)_8(CH_2)_5Z''$ and $(Tp)_7Ap(CH_2)_5Z''$ are attached to the poly(rA). The semi-dissociation temperatures of the complexes formed are, respectively, 41° and 27° C. The former forms 8 base pairs A.T., and the latter forms 7, but the disturbance in intercalation due to the absence of the last base pair considerably destabilizes the complex. By way of comparison, the compound $(Tp)_4(CH_2)_5Z''$ can form only 4 base pairs but gives rise to intercalation analogous to that of $(Tp)_8(CH_2)_5Z''$ at a semi-dissociation temperature of 31° C.

With the aid of the compounds according to the invention, it is also possible to detect accessible sequences in a protein-nucleic acid complex such as, for example, those found in ribosomes.

The compounds according to the present invention enable a DNA or RNA fragment containing a given sequence to be purified by affinity chromatography.

At the cellular level, the compounds according to the present invention enable cells having a given sequence (such as viruses) to be separated by flow cytofluorimetry, or may even enable the presence of a given sequence of DNA or RNA (for example of a virus) in a cell to be diagnosed (cytopathology).

In general, the compounds according to the present invention can be used as fluorescent probes and can replace the radioactive probes used hitherto. It is evident that a probe of this type has enormous advantages over radioactive probes. In particular, as has been stated, the oligonucleotide has a greater affinity for its complementary sequence due to the presence of the intercalating agent; in addition, the fluorescent agent can be detected much more rapidly than in the case of radioactive probes, and it has the advantage of being able to effect spatial resolution very easily.

With this type of probe, it is sufficiently easy to measure fluorescence quantitatively and thus to effect quantitative determination.

Finally, a not insignificant advantage of the probes according to the present invention with respect to those of the prior art is that it is not necessary to handle radioactive products.

The association of the compounds according to the present invention with nucleic acids can be monitored by various methods: absorption, fluorescence, circular dichroism or nuclear magnetic resonance.

Significant spectral modifications are observed in the absorption bands of the intercalating agent (significant hypochromism being able to reach 50%, displacement of the spectrum towards long wavelengths).

If the oligonucleotide contains a thymine sequence (T4, T8, T12), these spectral modifications reveal themselves only by fixation on the complementary sequence (polyA). No interaction at all is observed with polyU and polyC.

If the oligonucleotide sequence contains adenine (A5), only the polyU or polydT gives rise to characteristic spectral modifications. polyA has no effect.

The complexes formed with the compounds according to the present invention have been studied in order to demonstrate the influence of the various parameters on stability.

The stability may be measured by the semi-transition temperature of the complexes ($T_\frac{1}{2}$) when the temperature is increased. The table below compares these temperatures for oligonucleotides substituted either by an ethyl grouping or by a $(CH_2)_5$ branch bonded to the intercalating derivative of acridine. The values of $T_\frac{1}{2}$ were determined for a ratio of 1:1 (T:A) at an intercalating agent concentration of $5 \times 10^{-5}M$ and in a buffer of pH 7 containing $10^{-2}M$ sodium cacodylate and 0.1M NaCl.

| | |
|---|---|
| (T—)₁₂Et | 30° C. |
| (T—)₁₂(CH₂)₅Z" | 47° C. |
| (T—)₈Et | 9.5° C. |
| (T—)₈(CH₂)₅Z" | 41° C. |
| (T—)₄Et | <0° C. |
| (T—)₄(CH₂)₅Z" | 31° C. |

Stabilization of the complexes due to the presence of the intercalating agent is evident. The difference in temperature is the greater as the oligonucleotide is shorter.

Stabilization depends on the length of the branch used to attach the intercalating agent to the oligonucleotide, as the following $T_\frac{1}{2}$ show:

| | |
|---|---|
| (T—)₄(CH₂)₃Z" | 17° C. |
| (T—)₄(CH₂)₄Z" | 18° C. |
| (T—)₄(CH₂)₅Z" | 31° C. |
| (T—)₄(CH₂)₆Z" | 31° C. |

One branch of C₅ is thus sufficient to ensure good stabilization of the complex.

The stability of the complexes can also be determined by the free enthalpy of the reaction (kilocalories per mole) measured from the variation in $T_\frac{1}{2}$ with the oligonucleotide concentration.

| | |
|---|---|
| (T—)₁₂Et | 70 kcal.mole⁻¹ |
| (T—)₁₂(CH₂)₅Z" | 94 kcal.mole⁻¹ |
| (T—)₈Et | 51 kcal.mole⁻¹ |
| (T—)₈(CH₂)₅Z" | 73 kcal.mole⁻¹ |
| (T—)₄Et | not measurable |
| (T—)₄(CH₂)₅Z" | 39 kcal.mole⁻¹ |

The presence of the intercalating agent thus allows a gain of 20 to 30 kilocalories per mole of attached oligonucleotide.

The following examples are intended to illustrate other characteristics and advantages of the present invention, however without, of course, limiting it in any way.

In the description, the followiing condensed representation of the nucleotides is used:

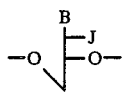

which corresponds to the expanded formula:

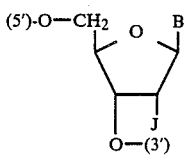

on which the ends (3') and (5') have been mentioned.

The abbreviations below are used in the present description:

| | |
|---|---|
| ODN | oligodeoxyribonucleotide |
| Ar | parachlorophenyl |
| CNEt | β-cyanoethyl |
| Me | methyl |
| Et | ethyl |
| MMTr | monomethoxytrityl |
| DMTr | dimethoxytrityl |
| Tr | trityl |
| MST | mesitylenesulfonyl tetrazolide |
| DMT | dimethyl-1,5-tetrazole |
| T | thymidine |

Z'

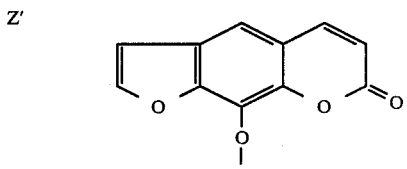

Z"

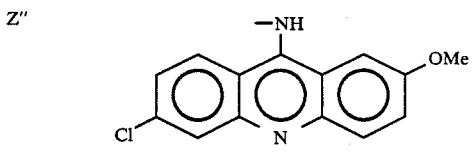

| | |
|---|---|
| TEA | triethylamine |
| TLC | thin layer chromatography |

In the formulae (DMTr) T∓T∓T∓T—Ar, the phosphodiester bond is represented by a line and the phosphotriester bond is represented by the symbol (∓), each phosphate being protected by the p-chlorophenyl group (Ar).

EXAMPLE I (DMTr) T∓(CH₂)₃ Z'

(1)

Pyridinium 5'-O-(dimethoxytrityl)-thymidine-3'(p-chlorophenylphosphate)

(a) 3 equivalents of methyl p-chlorophenyl chlorophosphate (prepared by the action of chlorine on dimethyl p-chlorophenyl phosphite) are added to a solution of 9 equivalents of 1,5-dimethyl-tetrazole (DMTe) in anhydrous pyridine at −20° C., with stirring; when the addition has ended, stirring is continued for 1 hour at the ambient temperature, and a solution of 1 equivalent of 5'-O-(dimethoxytrityl)-thymidine (J. Amer.

Chem. Soc., 1963, 85, 3821) in pyridine is added at −10° C. After a reaction time of some hours at the ambient temperature, ice-water is then added and the diester is extracted with chloroform; the chloroform solution is then dried and concentrated in vacuo. The diester, which is obtained in the form of a solution in pyridine, is virtually pure for use in the following stages. The yield of this reaction, based on the nucleoside, is virtually quantitative. TLC on silica gel; isoPrOH/TEA/H$_2$O (85:5:10, v/v), Rf~0.5.

(b) The same result is obtained if the methyl p-chlorophenyl chlorophenyl chlorophosphate is replaced by methyl p-chlorophenyl bromophosphate (Tetrahedron Letters, 1980, 21, 2063).

(2)

A solution of 0.25 mmol of the diester prepared above, 0.2 mmol of 8-(ω-hydroxypropoxy)-psoralen and 0.4 mmol of mesitylenesulfonyltetrazole (MST) (Nucleic Acids Res., 1977, 4, 353) in 1.5 ml of anhydrous pyridine is reacted at the ambient temperature for 2 hours, with stirring; 0.5 ml of ice-water is then added and stirring is continued at the same temperature for 20 minutes. The solution is concentrated in vacuo and the residue is taken up in chloroform; the organic phase is washed with 2×1 ml of an aqueous 5% strength solution of NaHCO$_3$ and dried over Na$_2$SO$_4$. After the solvent has been driven off in vacuo, the product obtained is purified over a silica gel column (eluant: CH$_2$Cl$_2$/MeOH).

The yield from the preparation is of the order of 80%, based on the psoralen derivative.

TLC: silica gel 60F254; solvent: CH$_2$CL$_2$, MeOH (9:1, v/v), Rf≃0.73.

EXAMPLES II AND III (DMTr)T∓(CH$_2$)$_n$Z''

By following the procedure as in Example 1 and replacing the 8-(ω-hydroxypropoxy)-psoralen with 2-methoxy-6-chloro-9-(ω-hydroxypropylamino)-acridine or with 2-methoxy-6-chloro-9-(ω-hydroxypentylamino)-acridine, the following compounds were prepared:

| Examples | n | Yield | Silica gel; 80:20 v/v | Rf (TLC) CH$_2$Cl$_2$/MeOH 90:10 v/v |
|---|---|---|---|---|
| II | 3 | ~85% | ~0.58 | |
| III | 5 | ~85% | ~0.60 | 0.36 |

EXAMPLE IV

Z''(CH$_2$)$_5$∓T∓CNEt (1)

Ar—T∓CNEt

The procedure followed is as in Example I-1, the 5'-O-(dimethoxytrityl)-thymidine being replaced by thymidine-3'-(p-chlorophenylβ-cyanoethyl phosphate) (Biochimie, 1981, 63, 775); after the product has been extracted with chloroform, the solvent and the pyridine are driven off in vacuo, the residue is taken up in ether and the white solid obtained is washed several times with the same solvent.

Yield: 90–95%.

TLC: silica gel; CH$_2$Cl$_2$ MeOH (85:25, v/v), Rf~0.32.

(2)

Coupling

A mixture of 1 equivalent of the nucleoside diphosphate prepared above (Example IV-1), 1.5 equivalents of 2-methoxy-6-chloro-9-(ω-hydroxypentylamino)-acridine, 2 equivalents of mesitylenesulfonyl chloride and 6 equivalents of tetrazole in pyridine is reacted at the ambient temperature for 2 hours. After the excess coupling reagent has been destroyed by addition of ice-water, the product is subsequently extracted with chloroform and purified over silica gel using CH$_2$Cl$_2$/MeOH mixtures (99:1 to 90:10, v/v). The product is obtained in the form of a yellow solid; the yield of the preparation is 82%.

TLC: silica gel, CH$_2$Cl$_2$/MeOH (9:1, v/v), Rf~0.21.

EXAMPLE V

Z''(CH$_2$)$_5$∓T∓T(Bz)

(1)

Z''(CH$_2$)$_5$∓T—Ar

The compound from Example IV-2 is treated with a solution of Et$_3$N-pyridine (1:2 v/v) (1 ml per mmol of triester (Nucleic Acids Res., 1976, 3, 3397) at the ambient temperature for several hours. After the solvents have been driven off in vacuo, the yellow solid obtained is subsequently washed with ether.

Yield ~88%

TLC: silica gel; iso-PrOH/Et$_3$N,H$_2$O (85:5:10, v/v), Rf~0.63.

(2)

The procedure followed is as in Example IV-2, using one equivalent of Z''(CH$_2$)$_5$∓T—Ar, 3 equivalents of 3'-benzoylthymidine and 10 equivalents of MST, and the product is obtained in the form of a yellow solid in a yield of 75%.

TLC: silica gel; CH$_2$Cl$_2$/MeOH (9:1, v/v), Rf~0.25.

EXAMPLE VI (DMTr) T∓T∓T∓T∓(CH$_2$)$_3$ Z'

(1)

(DMTr) T∓T—Ar 0.3 mmol of the dinucleotide (DMTr) dT∓T∓CNEt (Biochimie, 1981, 775) is treated with 5 ml of a solution of pyridine/triethylamine (2:1, v/v) at the ambient temperature for several hours. The solvent is driven off in vacuo and the solid obtained is washed with ether.

Yield~90%.

(2)

(DMTr) T∓T∓T∓T∓CNEt

The dinucleotide (DMTr)T∓T∓CNEt (0.2 mmol) is treated with benzenesulfonic acid (2% strength solution in chloroform/methanol (7.3, v/v) (3 ml) at 0° C. for 15 minutes (Nucleic Acids Res., 1977, 4, 353). The mixture is taken up in 40 ml of chloroform and the chloroform mixture is washed with a 5% strength aqueous solution of NaHCO$_3$, dried over Na$_2$SO$_4$ and concentrated in vacuo. 0.25 mmol of the dinucleotide prepared according to VI-1 is added to this residue; after the mixture has been dried by evaporation with pyridine, 3 ml of anhydrous pyridine are added to the residue followed by 0.6 mmol of MST and the reaction mixture is stirred at the ambient temperature for 2 hours. The excess coupling reagent is then destroyed by addition of ice-water and the preparation is completed as in Example I-2, replacing the mixture of $CH_2Cl_2/MeOH$ by the system $CH_2Cl_2$/water acetone (43:2:55, v/v). The yield of the preparation is 75%.

TLC: silica gel; $CH_2Cl_2/MeOH$ (9:1, v/v), Rf~0.50.

(3)

(DMTr) T∓T∓T∓T—Ar

The procedure followed is as in Example VI-1 using the tetranucleotide prepared according to VI-2, and the product is obtained in the form of a solid in a yield of the order of 80%.

(4)

(DMTr) T∓T∓T∓T∓(CH$_2$)$_3$ Z'

1 equivalent of (DMTr)T∓T∓T∓T—Ar, 1.3 equivalents of 8-(ω-hydroxypropoxy)-psoralen and 3 equivalents of MST are reacted in solution in anhydrous pyridine at the ambient temperature for 2 hours and the preparation is completed as in Example VI-2. Yield=72%.

TLC: silica gel; $CH_2Cl_2/MeOH$ (90:10, v/v), Rf~0.37.

EXAMPLE VII (DMTr) T∓T∓T∓(CH$_2$)$_5$ Z''

(1)

T∓(CH$_2$)$_5$ Z''

The compound (DMTr) T∓(CH$_2$)$_5$ Z'' from Example III is treated with 80% strength acetic acid at the ambient temperature for 1 hour 30 minutes; after the acetic acid has been driven off by coevaporation with ethanol, the product is subsequently purified over silica gel.

Yield: 86%.

TLC: silica gel; $CH_2Cl_2/MeOH$ (90:10, v/v), Rf=0.14.

(2)

(DMTr) T∓T∓T∓(CH$_2$)$_5$ Z''

A mixture of (DMTr) T∓T—Ar (1.2 equivalents) (Example VI-1), T∓(CH$_2$)$_5$ Z'' (1 equivalent) (prepared as above) and MST (2 equivalents) is reacted in anhydrous pyridine at the ambient temperature for 2 hours, with stirring; the preparation is then completed as in Example VI-2. Yield=78%.

TLC: silica gel; $CH_2Cl_2/MeOH$ (90:10, v/v), Rf=0.41.

EXAMPLE VIII (DMTr) T∓T∓T∓T∓(CH$_2$)$_5$ Z''

The procedure followed is as in Example VI-4 using 2-methoxy-6-chloro-9-(ω-hydroxypentylamino)-acridine (1.5 equivalents) instead of the psoralen derivative, and the desired product is obtained in a yield of 87%.

TLC: silica gel; $CH_2Cl_2/MeOH$ (90:10, v/v), Rf=0.37.

EXAMPLE IX

Z'(CH$_2$)$_3$∓T∓T∓T∓T—Ar (1)

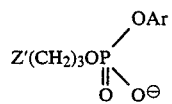

Methyl p-chlorophenyl bromophosphate (3 equivalents) is added to an excess of anhydrous pyridine (~50 equivalents) at −20° C., with stirring, stirring is continued at the ambient temperature for 15 minutes and 8-(ω-hydroxypropoxy)-psoralen (1 equivalent) is then added; the reaction is left at the ambient temperature for 2 hours and, after the usual treatment, the diester is purified over a silica gel column using successive mixtures of $CH_2Cl_2/MeOH$ (90:10, 85:15 and 75:25, v/v).

Yield~75%

TLC: silica gel; $CH_2Cl_2/MeOH$ (85:15, v/v), Rf=0.24.

(2)

T∓T∓T∓T∓CNEt

The totally protected tetranucleotide (1 equivalent) (Example VI-2) is treated with a 2% strength solution of benzenesulfonic acid in $CH_2Cl_2/MeOH$ (7:3, v/v) (~4 equivalents). The mixture is diluted with chloroform, washed several times with a 5% strength aqueous solution of $NaHCO_3$, dried over $Na_2SO_4$ and concentrated in vacuo; the solid obtained is then washed several times with ether. The yield of the preparation is 82%.

(3)

Z'(CH$_2$)$_3$∓T∓T∓T∓T∓CNEt

The coupling was carried out in anhydrous pyridine in the presence of the diester IX-1 (1.3 equivalents), T∓T∓T∓T∓CNEt (1 equivalent) and MST (2.5 equivalents). The preparation is then completed as in Example VI-2 by purifying the product over silica gel using successive mixtures of the solvents $CH_2Cl_2/H_2O$ acetone (43:2:55 and 32:3:65, v/v). Yield~55%.

TLC: silica gel; $CH_2Cl_2/MeOH$ (90:10, v/v), Rf~0.31.

(4)

Decyanoethylation

The totally protected compound (Example IX-3) is treated according to Example V-1. Yield~80%.

TLC: silica gel; $CH_2Cl_2/MeOH$ (85:15, v/v), Rf~0.64.

EXAMPLE X

Z'(CH$_2$)$_3$∓T∓T∓T∓T∓(CH$_2$)$_3$ Z'

(1)

Ar—T∓T∓T∓T∓CNEt

The procedure followed is as in Example IV-1, the mononucleotide T∓CNEt being replaced by the tetranucleotide T∓T∓T∓T∓CNEt; and the pyridinium salt is obtained in the form of a white solid. Yield~92%.

TLC: silica gel; $CH_2Cl_2/MeOH$ (75:25, v/v), Rf~0.47.

(2)

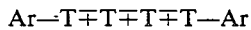

The tetranucleotide Ar—T∓T∓T∓T∓CNEt is used as the starting material and the procedure followed is as in Example VI-1, to give the product in the form of a white solid in a yield of 90%.

TLC: silica gel; isoPrOH/TEA/H₂O (85:5:10, v/v), Rf~0.12.

(3)

The coupling is carried out in anhydrous pyridine using 1 equivalent of the tetranucleotide 3′,5′-bis-(arly-phosphate) Ar—T∓T∓T∓T—Ar, 4 equivalents of 8-(ω- hydroxypropoxy)-psoralen and 6 equivalents of MST and following the procedure as in Example IX-3; the product is obtained in the form of a white solid.

TLC: silica gel; CH₂Cl₂/MeOH (9:1, v/v), Rf~0.5.

EXAMPLE XI

Z″(CH₂)₅∓T∓T∓T∓T∓(CH₂)₅ Z″

The procedure followed was according to Example X-3, using 2-methoxy-6-chloro-9-(ω-hydroxypentylamino)-acridine, and the product was obtained in the form of a yellow solid.

TLC: silica gel; CH₂Cl₂/MeOH (88:12, v/v), Rf~0.27.

EXAMPLE XII

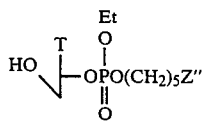

(1)

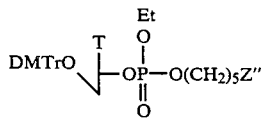

1 equivalent of (DMTr) T∓(CH₂)₅ Z″ (Example III) is added to a $6.10^{-4}$ molar solution of cesium fluoride (5 equivalents) in a mixture of EtOH/CH₃CN (50:50, v/v) at the ambient temperature, with stirring; stirring is then continued at the same temperature for 2 hours and the product is purified over silica gel using the solvent system CH₂Cl₂/EtOH (99:1 to 93:7, v/v). The product is obtained in the form of a yellow solid.

Yield=85%.

TLC: silica gel; CH₂Cl₂/MeOH (90:10, v/v), Rf~0.22.

(2)

Detritylation was carried out with acetic acid according to Example VII-1. Yield=78%.

TLC: silica gel; CH₂Cl₂/MeOH (90:10, v/v), Rf~0.1.

EXAMPLE XIII

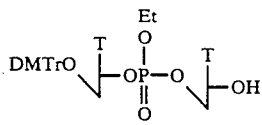

(1)

(DMTr) T∓T (a) A mixture of pyridinium 5′-O-(dimethoxytrityl)-thymidine-3′-(p-chlorophenyl phosphate) (Example I-1) (1 equivalent), thymidine (1.5 equivalents), tetrazole (6 equivalents) and mesitylenesulfonyl chloride (1.5 equivalents) in anhydrous pyridine is reacted at the ambient temperature for 1 hour 30 minutes, with stirring. The preparation is completed as in Example I-2 and the product is purified over silica gel using the system CH₂Cl₂/EtOH (99:1 to 94:6, v/v). The product is obtained in stereoisomeric form; the yield of the preparation is 78%.

TLC: silica gel; CH₂Cl₂/MeOH (90:10, v/v), 1 spot: Rf~0.36; CH₂Cl₂/THF (5:4, v/v), 2 spots: Rf=0.48–0.42.

(b) The isomers were separated by preparative chromatography on plates (silica gel 60 F 254, solvent CH₂Cl₂/THF (5:4, v/v).

TLC: silica gel; CH₂Cl₂/THF (5:4, v/v).

α isomer Rf=0.48.

β isomer Rf=0.42.

(2)

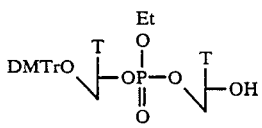

(a) The procedure followed is as in Example XII-1, the compound (DMTr)T∓(CH₂)₅Z″ being replaced by the stereoisomer (DMTr) T∓T (or by its α isomer or by its β isomer), and the ethyl ester is obtained in stereoisomeric form in a yield of 83%.

TLC: silica gel; CH₂Cl₂/MeOH (90:10, v/v), 1 spot: Rf~0.27; CH₂Cl₂/THF (5:4, v/v), 2spcts: Rf=0.32–0.24.

(b) The isomers were separated as above by preparative chromatography on plates.

TLC: silica gel; CH₂Cl₂/THF (5:4, v/v).

α isomer Rf=0.32.

β isomer Rf=0.24.

EXAMPLE XIV

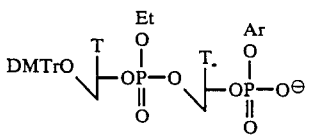

(1)

The procedure followed is as in Example IV-I, the nucleotide T∓CNEt being replaced by the compound

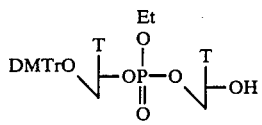

and the product is obtained in the form of the pyridinium salt in a yield of 90%.

TLC: silica gel; isoprOH/TEA/H₂O (85:5:10, v/v), Rf = 0.52.

EXAMPLE XV

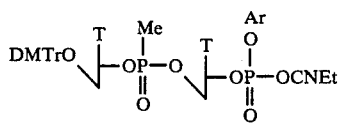

(1)

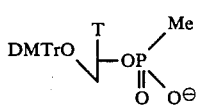

A mixture of 5'-O-(dimethoxytrityl)-thymidine (1 equivalent) and methylphosphonic anhydride (6 equivalents) (Russian Pat. No. 226,606 of 9/1/67) in pyridine is reacted overnight at the ambient temperature; the preparation is then completed as in Example I-1 and the product is purified over silica. Yield = 85%.

TLC: silica gel; isoprOH/Et₃N/H₂O (85:5:10, v/v), Rf~0.4.

(2)

The coupling of the nucleoside 3'-methyl-phosphonate XV-1 (1.5 equivalents) with thymidine-3'-(p-chlorophenyl β-cyanoethyl phosphate) (1 equivalent) is carried out in the presence of MST (3 equivalents) and the preparation is completed as in Example VI-2. Yield = 60%.

TLC: silica gel; CH₂Cl₂/MeOH (87:13, v/v), Rf = 0.58–0.61.

EXAMPLE XVI

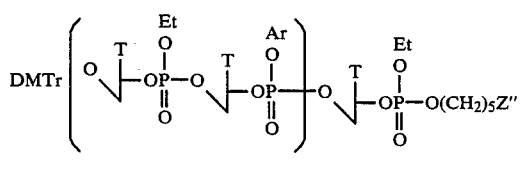

(1)

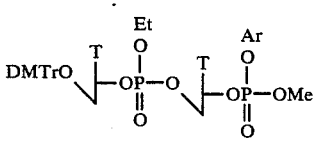

Methyl p-chlorophenyl bromophosphate (3 equivalents) is added to a solution of

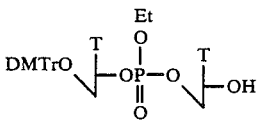

(1 equivalent), prepared according to Example XIII-2a, and 1-methyl-imidazole (6 equivalents) in acetonitrile at −20° C., with stirring, and stirring is continued at the ambient temperature for 30 minutes. After the excess bromophosphate has been destroyed by addition of water, the product is extracted with chloroform and purified over silica gel. Yield = 75%.

TLC: silica gel; CH₂Cl₂/MeOH (9:1, v/v), Rf~0.53.

(2)

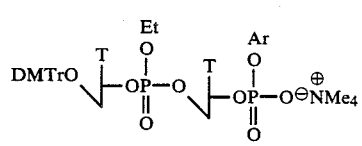

The dinucleotide prepared according to Example XVI-1 is treated with a 20% strength solution of trimethylamine in acetonitrile at the ambient temperature for 1 to 2 hours; the solvent is driven off in vacuo and the product is obtained in the form of the tetramethylammonium salt.

(3)

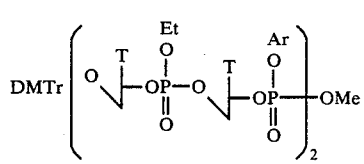

The procedure followed is as in Example VI-2, the compound (DMTr) T∓T∓CNEt being replaced by the compound prepared according to Example XVI-1 and the dinucleotide VI-1 being replaced by the compound XVI-2, and the tetranucleotide was prepared.

TLC: silica gel; CH₂Cl₂/MeOH (9:1, v/v), Rf~0.43.

(4)

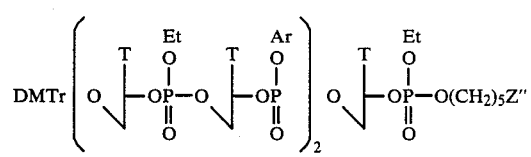

The tetranucleotide XVI-3 (1 equivalent), demethylated according to Example XVI-2, is then coupled with the mononucleotide (1 equivalent) prepared according to Example XII-2 in the presence of MST (2 equivalents); the preparation is completed as in Example VI-2.

TLC: silica gel; CH₂Cl₂/MeOH (85:15, v/v), Rf≃0.39.

EXAMPLE XVII

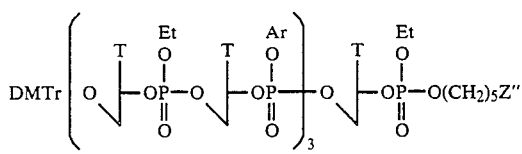

(1)

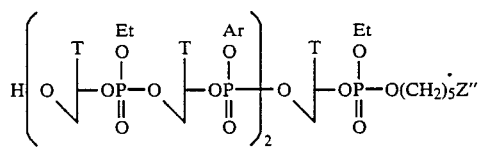

(2)

The procedure followed was as in Example IX-2, using the pentanucleotide XVI-4 as the starting material, and the product was obtained in the form of a yellow solid.

TLC: silica gel; CH$_2$Cl$_2$MeOH (85;15, v/v), Rf~0.26.

(2)

The pentanucleotide XVII-1 (1 equivalent) is coupled with the dinucleotide XVI-2 (1.5 equivalents) in the presence of MST (3 equivalents); the preparation is then completed as in Example VI-2.

TLC: silica gel; CH$_2$Cl$_2$/MeOH (85:15, v/v), Rf~0.35.

EXAMPLE XVIII

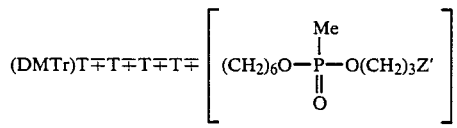

(1)

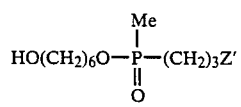

Methyl dichlorophosphonate (1.1 equivalents) is added to a solution of 1-hydroxy-benzotriazole (2.2 equivalents) and pyridine (2.2 equivalents) in tetrahydrofuran at 0° C., with stirring, and stirring is continued at 20° C. for 1 hour. 8-(ω-hydroxypropoxy)-psoralene (1 equivalent) is added to this mixture after a reaction time of 1 hour at the ambient temperature, hexane-1,6-diol (4 equivalents) and N-methylimidazole (4 equivalents) are then added and stirring is continued at the ambient temperature for 3 hours. After extraction with chloroform and washing with water, the product is subsequently purified over silica gel. The yield of the preparation is 62%.

TLC: silica gel; CH$_2$Cl$_2$/MeOH (9:1, v/v), Rf~0.32.

(2)

The procedure followed was according to Example VI-4, using the compound prepared above (Example XVIII-1) as the starting material, and the protected product was prepared, and was purified over silica gel with the system CH$_2$Cl$_2$/H$_2$O/acetone 46:1.5:52.5 and 43:2:55, v/v).

Yield ~75%.

TLC: silica gel; CH$_2$Cl$_2$/MeOH (9:1, v/v), Rf~0.64.

EXAMPLE XIX

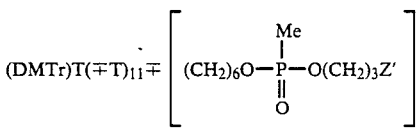

(1)

(DMTr) T (∓T)$_7$∓CNEt

A mixture of the diester (1.2 equivalents) prepared according to Example VI-3, the triester (1 equivalent) prepared according to Example IX-2 and MST (3 equivalents) is reacted at the ambient temperature for 2 hours; the preparation is then completed as in Example VI-2.

TLC: silica gel; CH$_2$Cl$_2$/MeOH (9:1, v/v), Rf~0.61.

(2)

(DMTr) T (∓T)$_6$∓T—Ar

The procedure followed was according to Example VI-1, using the compound (DMTr)T(+T)$_7$+CNEt as the starting substance, and the diester was obtained in the form of a white solid.

(3)

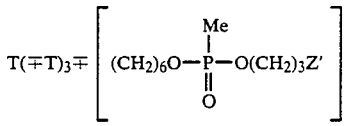

The procedure followed was as in Example IX-2, using the compound prepared according to Example XVIII-2 as the starting substance, and the product was obtained in the form of a white solid.

(4)
Coupling

The procedure followed was according to XIX-1, using the diester XIX-2 and triester XIX-3 as starting substances, and the protected dodecanucleotide was prepared, and was purified over silica gel with the system CH$_2$Cl$_2$/H$_2$O/acetone (20:5:75, v/v).

TLC: silica gel; CH$_2$Cl$_2$/MeOH (9:1, v/v), Rf~0.4.

EXAMPLE XX

Z"(CH$_2$)$_5$(∓T)$_8$(Bz)

(1)

Z"(CH$_2$)$_5$(∓T)$_4$∓CNEt

The procedure followed was as in Example VI-4, using the diester prepared according to Example X-1 (1 equivalent) and 2-methoxy-6-chloro-9-(ω-hydroxypentylamino)-acridine, and the product was obtained in the form of a yellow solid in a yield of 73%.

TLC: silica gel; CH$_2$Cl$_2$/MeOH (85:15, v/v), Rf~0.4.

(2)

Z"(CH$_2$)$_5$(∓T)$_4$—Ar

The totally protected tetranucleotide (XX-1) is treated according to Example V-1. Yield~85%.

TLC: silica gel; CH$_2$Cl$_2$/MeOH (85:15, v/v), Rf~0.11..

(3)

A mixture of Z"(CH$_2$)$_5$(∓T)$_4$—Ar (1 equivalent), T(∓T)$_3$(Bz) (1.2 equivalents) and MST (2 equivalents) is reacted in anhydrous pyridine at the ambient temperature for 2 hours, with stirring, and the preparation is completed as in Example VI-2.

TLC: silica gel; CH$_2$Cl$_2$/MeOH (85:15, v/v), Rf~0.45.

EXAMPLE XXI (DMTr)(T∓)$_4$(CH$_2$)$_4$Z"

The procedure followed is as Example VI-4 using 2-methoxy-6-chloro-9-(ω-hydroxybutylamino-acridine (1.5 equivalents) instead of the psoralene derivative, and the totally protected product is obtained in a yield of 82%.

TLC: silica gel; CH$_2$Cl$_2$/MeOH (90:10, v/v), Rf=0.18.

EXAMPLE XXII (DMTr)(T∓)$_8$(CH$_2$)$_5$Z"

(1)

(T∓)$_4$(CH$_2$)$_5$Z"

The product is obtained by detritylation of the compound of Example VIII.

TLC: silica gel; CH$_2$Cl$_2$/MeOH (85:15, v/v), Rf~0.3.

(2)

1 equivalent of (T∓)$_4$(CH$_2$)$_5$Z", 1.2 equivalents of (DMTr)(T∓)$_3$T—Ar (Example VI-3) and 2.5 equivalents of MST are reacted in solution of pyridine at the ambient temperature for 1 hour, and the preparation is completed as in Example VI-2, using the system CH$_2$Cl$_2$/H$_2$O/acetone (20:5:75, v/v). Yield 73%.

TLC: silica gel; CH$_2$Cl$_2$/MeOH (85:15, v/v), Rf≃0.37.

EXAMPLE XXIII (DMTr)(T∓)$_8$(CH$_2$)$_6$Z"

The procedure followed is according to XXII-2 using the diester (DMTr)T(∓T)$_6$∓T—Ar from Example XIX-2 (1 equivalent), 2-methoxy-6-chloro-9-(ω-hydroxyhexylamino)-acridine (2 equivalents) and MST (2 equivalents) as the starting substances, and the product was obtained in a yield of 72%.

TLC: silica gel; CH$_2$Cl$_2$/MeOH (85:15, v/v), Rf~0.38.

EXAMPLE XxIv (DMTr)(T∓)$_{12}$(CH$_2$)$_5$Z"

The procedure followed was as in Example XXII-2, using the compound (DMTr)T(∓T)$_6$∓T—Ar (Example XIX-2) (1 equivalent) and the compound (T∓)$_4$(CH$_2$)$_5$Z"(Example XXII-1) (1.2 equivalents), and the totally protected dodecanucleotide was obtained in a yield of 68%.

TLC: silica gel; CH$_2$Cl$_2$/MeOH (85:15, v/v), Rf~0.32.

EXAMPLE XXV

Z"(CH$_2$)$_5$∓(T∓)$_8$(CH$_2$)$_5$Z"

(1)

Ar—(T∓)$_8$CNEt

The (T∓)$_8$CNEt prepared by detritylation of (DMTr)(T+)$_8$CNEt (Example XIX-1) is phosphorylated as in Example IV-1.

TLC: silica gel; CH$_2$Cl$_2$/MeOH (85:15, v/v), Rf~0.12; CH$_2$Cl$_2$/MeOH (75:25, v/v), Rf~0.6.

(2)

Ar—(T∓)$_7$T—Ar

The procedure followed is as in Example VI-1, using Ar—(T∓)$_8$CNEt as the starting substance, and the product is obtained in the form of a solid.

TLC, silica gel; CH$_2$Cl$_2$/MeOH (75:25, v/v), Rf~0.15.

(3)

The procedure followed is as in Example XXII-2, using Ar—(T∓)$_7$T—Ar (1 equivalent), 2-methoxy-6-chloro-9-(ω-hydroxypentylamino)-acridine (3 equivalents) and MSTe (sic) (5 equivalents), and the octanucleotide was obtained.

TLC: silica gel; CH$_2$Cl$_2$/MeOH (85:15, v/v), Rf~0.3.

EXAMPLE XXVI

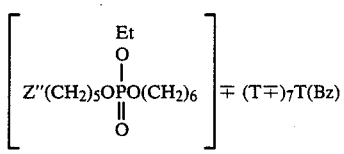

(1)

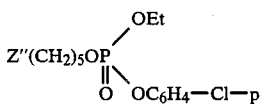

P-chlorophenyl ethyl bromophosphate (2 equivalents) is added to a solution of 2-methoxy-6-chloro-9-(ω-hydroxypentylamino)-acridine (1 equivalent) in pyridine at −10° C.; after 20 minutes at the ambient temperature, the excess bromophosphate is destroyed by addition of water and the product is extracted with chloroform and purified over silica.

TLC: silica gel; CH$_2$Cl$_2$/MeOH (90:10, v/v), Rf~0.42.

(2)

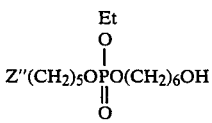

A mixture of the compounds

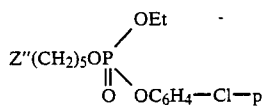

(1 equivalent), hexane-1,6-diol (6 equivalents) and cesium fluoride (5 equivalents) in acetonitrile is reacted at the ambient temperature for 24 hours and the product is purified over silica gel.

TLC: silica gel; CH₂Cl₂/MeOH (90:10, v/v), Rf~0.23.

(3)

Ar—(T∓)₇T(Bz)

(T∓)₇T(bz) obtained by detritylation of (DMTr)(T∓)₇T(bz) is phosphorylated according to Example IV-1.

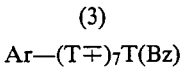

TLC: silica gel; CH₂Cl₂/MeOH (85:15, v/v), Rf~0.14.

(4)

The procedure followed was as in Example XXII-2, using

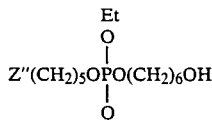

(1.5 equivalents), Ar—(T+)₇T(Bz) (1 equivalent) and MST (2.5 equivalents) as the starting substances, and the product was obtained.

TLC: silica gel; CH₂Cl₂/MeOH (90:10, v/v), Rf~0.2.

EXAMPLES XXVII AND XXVIII

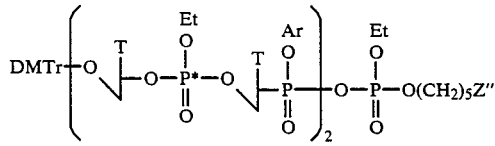

Isomer α: The procedure followed is as in Example XVI, replacing the diastereoisomer

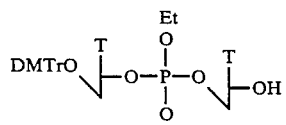

by the α isomer (Example XIII-2b) (TLC: silica gel; CH₂Cl₂/THF (5:4, v/v), Rf~0.32). The pentanucleotide of which the two internucleotidic ethyl phosphate groups are in the form of the α isomer was obtained.

TLC: silica gel; CH₂Cl₂/MeOH (85:15, v/v), Rf 0.39.

β Isomer: The procedure followed was as above, using the β isomer of the dinucleotide monophosphate

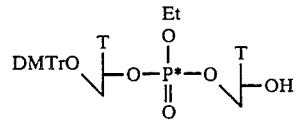

(Example XIII-2b), (TLC: silica gel; CH₂Cl₂/THF (5:4, v/v), Rf≃0.24) as the starting substance, and the pentanucleotide in which the two internucleotidic ethyl phosphate groups are in the form of the β isomer was obtained.

TLC: silica gel; CH₂Cl₂/MeOH (85:15, v/v), Rf 0.39.

EXAMPLE XXIX

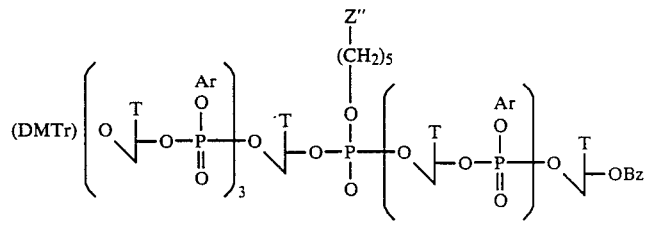

(1)

Ammonium 5'-O-(dimethoxytrityl)-thymidine-3'-phosphate.

Methyl dichlorophosphate (4 equivalents) is added to pyridine (~1,000 equivalents) at −20° C., with stirring, and after 15 minutes 5'-O-(dimethoxytrityl)thymidine (1 equivalent) is added to this mixture and stirring is continued for 30 minutes. After the excess phosphorylation reagent has been destroyed by addition of water, the product is extracted with chloroform and purified over silica (solvent: isoPrOH/NH₄OH/H₂O (7:2:1, v/v)).

Yield~75%.

TLC: silica gel; IsoProOH/NH₄OH/H₂O (7:2:1, v/v), Rf~0.65.

(2)

(DMTr)T—(T∓)₃T(Bz)

A solution of triethylammonium 5'-O-(dimethoxytrityl)-thymidine-3'-phosphate (2 equivalents) (obtained by coevaporation of the ammonium salt with a solution of triethylamine in pyridine), (T∓)₃T(Bz) (1 equivalent) and 2,4,6-triisopropylbenzenesulfonyl chloride (3 equivalents) in pyridine is reacted at the ambient temperature for 3 hours; after the usual treatment, the product is subsequently purified over silica (preparative plate) using the solvent system CH₂Cl₂/MeOH (85:15, v/v).

Yield~78%.

TLC: silica gel; CH₂Cl₂/MeOH (80:20, v/v), Rf~0.3.

(3)

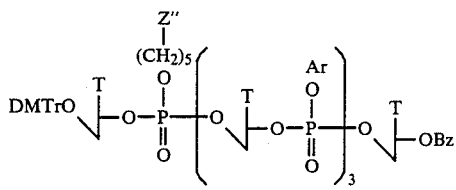

A solution of (DMTr)T-(T∓)₃T(Bz) (1 equivalent) prepared as above, 2-methoxy-6-chloro-9-(ω-hydroxypentylamino)-acridine (2 equivalents) and MST (5 equivalents) in pyridine is reacted at the ambient temperature for 6 hours and the preparation is completed as in Example XXII- 2. Yield ~65%.

TLC: silica gel; CH₂Cl₂/MeOH (85:15, v/v), Rf~0.33.

(4)

The compound

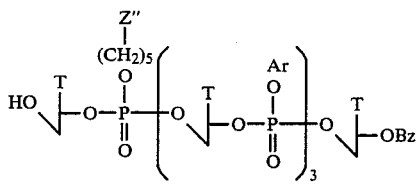

(1 equivalent) (TLC: silica gel; CH₂Cl₂/MeOH (85:15, v/v), Rf~0.2, prepared by detritylation of the compound from Example XXIX-3) is coupled with the diester (DMTr)T∓T∓T—Ar (1.5 equivalents) in the presence of MST (2.5 equivalents) in pyridine and the preparation is subsequently completed as in Example XXII-2. Yield ~63%.

TLC: silica gel; CH₂Cl₂/MeOH (85:15, v/v), Rf~0.4.

EXAMPLE XXX

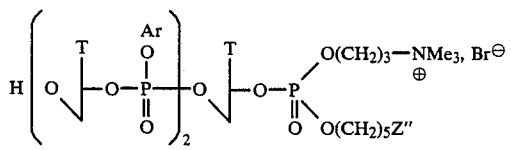

(1)

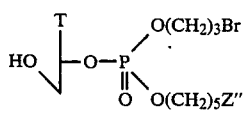

The procedure followed is as in Example XII, the ethanol being replaced by 3-bromo-propan-1-ol.

TLC: silica gel; CH₂Cl₂/MeOH (90:10, v/v), Rf=0.18.

(2)

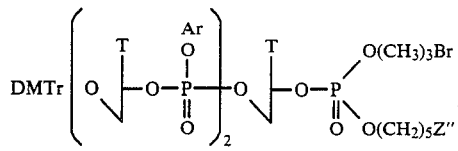

The product is obtained by coupling the dinucleotide (DMTr)T∓T—Ar (2 equivalents) with the mononucleotide (Example XXX-1) (1 equivalent) in the presence of MST (3 equivalents).

TLC: silica gel; CH₂Cl₂/MeOH (85:15, v/v), Rf≈0.21 and 0.27.

(3)

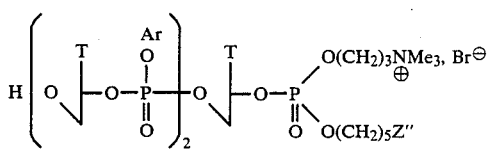

The trinucleotide

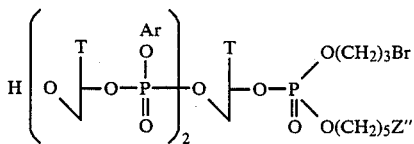

(TLC: silanised silica gel; acetone, water (16:6, v/v), Rf~0.5) (prepared by detritylation of the compound from Example XXX-2) is treated with a solution of trimethylamine in acetonitrile at the ambient temperature for some hours. After evaporation of the solvent, the product is obtained in the form of a yellow solid.

TLC: silanised silica gel; acetone, water (16:6, v/v), Rf≈0.05.

EXAMPLE XXXI

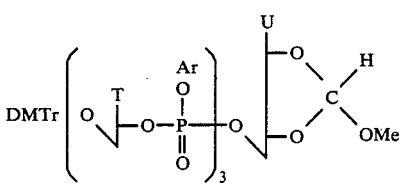

(1)

(DMTr)(T∓)₃CNEt

The procedure followed was as in Example VI-2, the dinucleotide (DMTr)T∓T—Ar being replaced by the mononucleotide (DMTr)T—Ar, and the detrinucleotide was prepared.

(2)

Ar—(T∓)₃CNEt (T∓)₃CNEt, prepared by detritylation of (DMTr)(T∓)₃CNEt, is phosphorylated according to Example IV-1.

TLC: silica gel; CH$_2$Cl$_2$/MeOH (90:10, v/v), Rf≃0; CH$_2$Cl$_2$/MeOH (80:20, v/v), Rf≃0.5.

(3)

Z″(CH$_2$)$_5$∓(T∓)$_3$CNEt.

By coupling the trinucleotide Ar-(T∓)$_3$CNEt (1 equivalent) with 2-methoxy-6-chloro-9-(ω-hydroxypentylamino-acridine (2 equivalents) in the presence of MST (3 equivalents), the totally protected trinucleotide was obtained in a yield of 70%.
TLC: silica gel; CH$_2$Cl$_2$/MeOH (90:10, v/v), Rf≃0.1; CH$_2$Cl$_2$/MeOH (85:15, v/v), Rf≃0.35.

(4)

The diester Z″(CH$_2$)$_5$∓(T∓)$_2$T—Ar (1 equivalent), prepared by decyanoethylation of Z″(CH$_2$)$_5$∓(T∓)$_3$CNEt according to Example VI-1 is coupled with 2′,3′-O-methoxymethylidene-uridine (2 equivalents) in the presence of MST (3 equivalents); after the usual treatment, the product is purified over silica gel.
TLC: silica gel; CH$_2$Cl$_2$/MeOH (90:10, v/v), Rf≃0.36; CH$_2$Cl$_2$/MeOH (85:15, v/v), Rf≃0.53.

EXAMPLE XXXII (DMTr)dbzA∓(CH$_2$)$_5$Z″

(1)

Pyridinium 5′-O-(dimethoxytrityl)-N-benzoyldeoxyadenosine-3′-(p-chlorophenyl phosphate)

The procedure followed was as in Example I-1a, using 5′-O-(dimethoxytrityl)-N-benzoyl-deoxyadenosine as the starting substance, and the product was prepared.
TLC: silica gel; isoPrOH/TEA/H$_2$O (85:5:10, v/v), Rf~0.5.

(2)

The procedure followed is as in Example I-2, the 8-(ω-hydroxypropoxy)-psoralene being replaced by 2-methoxy-6-chloro-9-(ω-hydroxypentylamino)-acridine and the diester derivative of thymine being replaced by the diester derivative of adenine. Yield≃80%.
TLC: silica gel; CH$_2$Cl$_2$/MeOH (90:10, v/v), Rf≃0.42.

EXAMPLE XXXIII (DMTr)danC∓(CH$_2$)$_5$Z″

The procedure followed was according to Example XXXII, using 5′-O-(dimethoxytrityl)-N-anisoyldeoxycytidine as the starting substance, and pyridinium 5′O-(dimethoxytrityl)-N-anisoyldeoxycytidine-3′-(p-chlorophenyl phosphate) (DMTr) danC-Ar[TLC, silica gel; isoPrOH/TEA H$_2$O (85:5;10, v/v), Rf~0.47] and the compound (DMTr)danC∓CH$_2$)$_5$Z″ were prepared. Yield≃80%
TLC: silica gel; (CH$_2$Cl$_2$/MeOH (90:10, v/v), Rf≃0.4.

EXAMPLE XXXIV (DMTr) dibG∓(CH$_2$)$_2$Z″

The procedure followed was according to Example XXXII, using 5′-O-(dimethoxytrityl)-N-isobutyryl-deoxyguanosine as the starting substance, and pyridinium 5′-O-(dimethoxytrityl)-N-isobutyryl-deoxyguanosine-3′-(p-chlorophenyl phosphate) (DMTr) dibG-Ar [TLC: silica gel, isoPrOH/TEA/H$_2$O (85:5:10, v/v), Rf~0.45] and the compound (DMTr)dibG∓(CH$_2$)$_5$Z″ were prepared.
Yield = 70%.
TLC: silica gel; CH$_2$Cl$_2$/MeOH (90:10, v/v), Rf≃0.43.

EXAMPLE XXXV (DMTr) d(bzA∓)$_5$ (CH$_2$)$_5$Z″

(1)

(DMTr)d(bzA∓)$_3$bz—A—Ar

The procedure followed was as in Examples VI-1, VI-2 and VI-3, using the dinucleotide (DMTr)dbzA∓bzA∓ CNEt (Biochimie, 1981, 775) as the starting substance, and the tetranucleotide was prepared.

(2)

The compound dbzA∓(CH$_2$)$_5$Z″ (1 equivalent) (obtained by detritylation of the compound (DMTr) dbzA∓(CH$_2$)$_5$Z‴, Example XXXII) is coupled with the tetranucleotide XXXV-1 (1.5 equivalents) in the presence of MST (3 equivalents); after the usual treatment, the product is purified over silica using successive systems of CH$_2$Cl$_2$/H$_2$O/acetone (46:2:52 and 40:2:58, v/v).
TLC: silica gel; CH$_2$Cl$_2$/MeOH (90:10, v/v), Rf≃0.16.

EXAMPLE XXXVI (DMTr)dbzA∓T∓bzA∓bzA∓BzA∓T∓T∓anC∓BzA∓anC∓(CH$_2$)$_5$Z″

(1)

(DMTr)dbzA∓T∓bzA∓bzA∓CNEt

The tetranucleotide was prepared using (DMTr)dbzA∓T—Ar (1.2 equivalents), dbzA∓bzA∓CNEt (2 equivalents) and MST (3 equivalents) as starting substances, and is purified over silica gel using systems of CH$_2$Cl$_2$/H$_2$O/acetone (52:2:46 and 43:2:55, v/v).
TLC: silica gel; CH$_2$Cl$_2$/MeOH (90:10, v/v), Rf~0.35.

(2)

(DMTr)dbzA∓T∓bzA∓bzA∓bzA∓T∓CNEt

The tetranucleotide from Example XXXVI-1, which is decyanoethylated by triethylamine according to Example VI-1, is then coupled with the dinucleotide dbzA∓T∓CNEt in the presence of MST. After the usual treatment, the product is purified over silica gel using the system CH$_2$Cl$_2$/H$_2$O/acetone (43:2:55, v/v).

(3)

(DMTr)dbzA∓anC∓(CH$_2$)$_5$Z″ danC∓(CH$_2$)$_5$Z″ (1 Equivalent) (obtained by detritylation of the compound (DMTr)danC∓(CH$_2$)$_5$Z″ according to Example VII-1) is coupled with the nucleotide prepared according to Example XXXII-1 (1.2 equivalents) in the presence of MST (3 equivalents), and, after the usual treatment, the product is purified over silica gel using successive systems of CH$_2$Cl$_2$/H$_2$O/acetone (59:1:40, 53:2:45 and 46:2:52).

(4)

(DMTr)dT∓anC∓bzA∓anC∓(CH₂)₅Z″

Coupling of the dinucleotide (DMTr)dT∓anC—Ar (1.2 equivalents) with the dinucleotide dbzA-∓anC∓(CH₂)₅Z″ (obtained by detritylation of the compound XXXVI-3) (1 equivalent) gives the tetranucleotide.

TLC: silica gel; $CH_2Cl_2/MeOH$ (90:10, v/v), Rf~0.42.

(5)

Coupling of the hexanucleotide (DMTr)dbzA∓T∓bzA∓bzA∓bzA∓T—Ar (1.2 equivalents) (obtained by decyanoethylation of the compound from Example XXXVI-2) with the tetranucleotide dT∓anC∓bzA∓anC∓(CH₂)₅Z″ (1 equivalent) (prepared by detritylation of the compound from Example XXXVI-4) gives the totally protected decanucleotide, which is purified over silica gel using successive systems of $CH_2Cl_2/H_2O$/acetone (63:1:36 and 32:3:65, v/v).

TLC: silica gel; $CH_2Cl_2/MeOH$ (90:10, v/v), Rf~0.24.

EXAMPLE XXXVII (DMTr)dbzA∓bzA∓T∓ibG∓ibG∓T∓bzA∓bzA∓bzA∓bzA∓T∓(CH₂)₅Z″

(1)

(DMTr)dbzA∓bzA∓bzA∓bzA∓T∓(CH₂)₅Z″

The tetranucleotide (DMTr)dbzA∓bzA∓bzA∓bzA—Ar (1 equivalent) (Example XXXV-1) is reacted with the mononucleotide T∓(CH₂)₅Z″ (1 equivalent) (Example VII-1) in the presence of MST (3 equivalents) in solution in pyridine at the ambient temperature for 2 hours and the preparation is completed as in Example XXXV-2.

Yield≃50%.

TLC: silica gel; $CH_2Cl_2/MeOH$ (90:10, v/v), Rf~0.18.

(2)

(DMTr)dT∓ibG∓ibG∓T∓CNEt

The procedure followed was as in Example XXXV-2, using (DMTr)dT∓ibG—Ar, and dibG∓T∓CNEt as the starting substances, and the tetranucleotide was obtained in a yield of 50%.

TLC: silica gel; $CH_2Cl_2/MeOH$ (90:10, v/v), Rf≃0.48.

(3)

(DMTr)dbzA∓bzA∓T∓ibG∓ibG∓T∓CNEt

The tetranucleotide dT∓ibG∓ibG∓T∓CNEt (1 equivalent) (prepared by detritylation of the compound XXXVII-2) is coupled with the dinucleotide (DMTr)dbzA∓bzA—Ar (1.3 equivalents) in the presence of MST (3 equivalents); after the usual treatment, the product is purified over silica using the system $CH_2Cl_2H_2O$ for)/acetone (43:2:55, v/v). Yield 52%.

TLC: silica gel; $CH_2Cl_2/MeOH$ (90:10, v/v), Rf=0.42.

(4)

The hexanucleotide (DMTr)dbzA∓bzA∓T∓ibG∓ibG∓T—Ar (1.2 equivalents) (prepared by decyanoethylatio of the compound XXXVII-3 according to Example VI-1) is coupled with the pentanucleotide dbzA∓bzA∓bzA∓bzA∓T∓(CH₂)₅Z″ (1 equivalent) (obtained by detritylation of the compound XXXVII-1) in the presence of MST (3 equivalents); after the usual treatment, the product is purified over silica using the system $CH_2Cl_2/H_2O$/acetone (32:3:65, v/v).

TLC: silica gel; $CH_2Cl_2/MeOH$ (90:10, v/v), Rf≃0.2.

EXAMPLE XXXVIII

Z′(CH₂)₃—T—T—T—(CH₂)₃Z′

The totally protected oligonucleotide prepared according to Example X is reacted with a molar solution of benzohydroxamic acid and of 1,8-diazabicyclo(5,4,-0)undec-7-ene(DBU) in anhydrous pyridine at the ambient temperature overnight, with stirring, using 10 equivalents of $$C_6H_5\underset{\underset{O}{\|}}{C}NHOH-DBU$$

per equivalent of arylated phosphoester to be deprotected. The reaction mixture is neutralized with DOWEX 50 (pyridinium form) and filtered and the resin is washed with a mixture of $H_2O/MeOH$ (1:1 v/v), and the solvent is driven off in vacuo. The product is subsequently purified over a DEAE Sephacel column using an elution gradient ($10^{-3}M$–0.5M) of $NH_4HCO_3$ in $H_2O$ MeOH (70:30, v/v).

TLC: silica gel; isoPrOH/NH₄si OH/H₂O (65:9:15, v/v), Rf~0.25.

EXAMPLE XXXIX

Z″(CH₂)₅—T—T—T—T—(CH₂)₅Z″

The procedure followed was as in Example XXXVIII, using the tetranucleotide prepared according to Example XI as the starting substance, and the product was isolated in the form of a yellow solid. TLC: silica gel; isoPrOH/NH₄OH/H₂O (65:9:15, v/v), Rf~0.4.

EXAMPLE XXXX

Z″(CH₂)₅—(T—)₈(CH₂)₅Z″

The octanucleotide Z″(CH₂)₅+(T+)₈(CH₂)₅Z″ (Example XXV) is de-protected as in Example XXXVIII. The product is purified over DEAE-Sephacel using an elution gradient ($5.10^{-2}M$–0.8M) of $NH_4HCO_3$ in $H_2O/MeOH$ (50:50, v/v).

TLC: silica gel; isoPrOH/NH₄OH/H₂O (85:9:25, v/v), Rf≃0.42.

EXAMPLES XXXXI to LVI

The dearylation is carried out as in Example XXXVIII; the residue obtained after evaporation of the solvent is treated with 80% strength acetic acid at the ambient temperature for 1 to 2 hours. The acetic acid is removed in vacuo by evaporation several times with ethanol; the residue is taken up in water and the aqueous phase is washed with ether. The products are then purified over DEAE-Sephacel using an elution gradient of $NH_4HCO_3$, in accordance with the number of charges ($10^{-3}M$–0.2M to $10^{-3}M$–1M).

| Example | Protected nucleotides | De-protected nucleotides | TLC Silica 60 F 254 | Rf | Solvent | Cellulose Rf |
|---|---|---|---|---|---|---|
| XXXXI | (DMTr)T∓(CH$_2$)$_3$Z' | T—(CH$_2$)$_3$Z' | CH$_2$Cl$_2$/MeOH (70:30, v/v) | 0.55 | | |
| XXXXII | (DMTr)T∓(CH$_2$)$_3$Z'' | T—(CH$_2$)$_3$Z'' | isoPrOH/NH$_4$OH,H$_2$O (65:9:15, v/v) | 0.70 | | |
| XXXXIII | (DMTr)T∓(CH$_2$)$_5$Z'' | T—(CH$_2$)$_5$Z'' | isoPrOH/NH$_4$OH,H$_2$O (65:9:15, v/v) | 0.71 | | |
| XXXXIV | (DMTr)T∓T∓T∓(CH$_2$)$_5$Z'' | T—T—T—(CH$_2$)$_5$Z'' | isoPrOH/NH$_4$OH,H$_2$O (65:9:15, v/v) | 0.45 | | |
| XXXXV | (DMTr)T∓T∓T∓T∓T∓(CH$_2$)$_3$Z' | T—T—T—T—T—(CH$_2$)$_3$Z' | isoPrOH/NH$_4$OH,H$_2$O (65:9:15, v/v) | 0.4 | EtOH/AcONH$_4$ (4:6, v/v) | 0.78 |
| XXXXVI | (DMTr)T∓T∓T∓T∓T∓(CH$_2$)$_5$Z'' | T—T—T—T—T—(CH$_2$)$_5$Z'' | isoPrOH/NH$_4$OH,H$_2$O (65:9:15, v/v) | 0.4 | | |
| XXXXVII | [structure with Ar, Et, P, T, (CH$_2$)$_5$Z'', DMTr] | [structure with H, Et, P, T, (CH$_2$)$_5$Z''] | isoPrOH/NH$_4$OH,H$_2$O (65:9:15, v/v) | 0.52 | | |
| XXXXVIII | [structure with Ar, Et, P, T, (CH$_2$)$_5$Z'', DMTr] | [structure with H, Et, P, T, (CH$_2$)$_5$Z''] | isoPrOH/NH$_4$OH,H$_2$O (65:9:15, v/v) | 0.43 | | |
| XXXXIX | (DMTr)T(∓T)$_3$∓[(CH$_2$)$_6$O—P(Me)—O(CH$_2$)$_3$Z'] | T—T—T—T—[(CH$_2$)$_6$O—P(Me)—O(CH$_2$)$_3$Z'] | | | | |
| L | (DMTr)T(∓T)$_{11}$∓[(CH$_2$)$_6$O—P(Me)—O(CH$_2$)$_3$Z'] | T(—T)$_{11}$—[(CH$_2$)$_6$O—P(Me)—O(CH$_2$)$_3$Z'] | | | | |
| LI | (DMTr)T(∓T)$_4$(CH$_2$)$_4$Z'' | T(—T)$_4$(CH$_2$)$_4$Z'' | isoPrOH/NH$_4$OH,H$_2$O (65:9:15, v/v) | 0.4 | | |
| LII | (DMTr)T(∓T)$_8$(CH$_2$)$_5$Z'' | T(—T)$_8$(CH$_2$)$_5$Z'' | isoPrOH/NH$_4$OH,H$_2$O (65:9:15, v/v) | 0.13 | | |
| LIII | (DMTr)T(∓T)$_8$(CH$_2$)$_6$Z'' | T(—T)$_8$(CH$_2$)$_6$Z'' | isoPrOH/NH$_4$OH,H$_2$O (65:9:15, v/v) | 0.13 | | |

| Example | Protected nucleotides | De-protected nucleotides | TLC Silica 60 F 254 | Rf | Cellulose Solvent | Rf |
|---|---|---|---|---|---|---|
| LIV | (DMTr)(T∓)₁₂(CH₂)₅Z″ | (T—)₁₂(CH₂)₅Z″ | (85:9:25, v/v) | 0.16 | | |
| LV | [structure shown, isomer] | [structure shown, isomer] | (65:9:15, v/v) | 0.54 | | |
| LVI | [structure shown, isomer] | [structure shown, isomer] | (65:9:15, v/v) | 0.54 | | |

EXAMPLE LVII

Z"(CH₂)₅(—T)₇—T

The dearylation of the compound Z"(CH₂)₅(∓T)₇∓T(Bz) is carried out according to Example XXXVIII; the residue obtained after evaporation of the solvent is treated with aqueous sodium hydroxide (0.25M) at the ambient temperature for 45 minutes. After the reaction mixture has been neutralized with an anionic resin in the pyridinium form, the product is purified over DEAE Sephacel [elution gradient $10^{-3}$M–0.9M on NH₄HCO₃ in H₂0/MeOH (70:30, v/v)].

TLC: silica gel; isoPrOH/NH₄OH/H₂O (65:9:15, v/v), Rf~0.13.

EXAMPLE LVIII

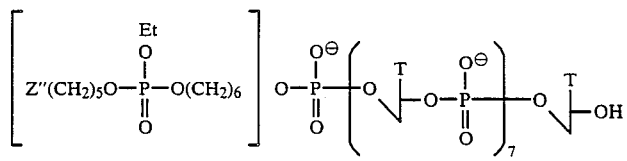

The procedure followed was as in Example LVII, the octanucleotide prepared according to Example XXVI being treated, and the product was obtained.

TLC: silica gel; isoPrOH/NH₄OH/H₂0 (65:9:15, v/v), Rf~0.13

EXAMPLE LIX

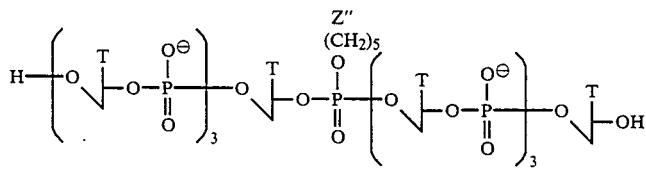

The dearylation of the compound of Example XXIX is carried out according to Example XXXVIII; the residue obtained after evaporation of the solvent is treated with aqueous sodium hydroxide (0.25M) at the ambient temperature for 45 minutes. After the reaction mixture has been neutralized with an anionic resin (pyridinium form) and the solvent has been driven off in vacuo, the residue is subsequently treated with 80% strength acetic acid and the preparation is completed as in Examples XXXXI to LVI.

TLC: silica gel; isoPrOH/NH₄OH/H₂O (65:9:15, v/v), Rf≈0.3.

EXAMPLE LX

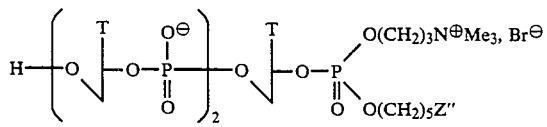

The dearylation of the compound

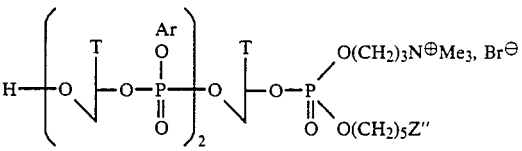

(Example XXX) is carried out as in Example XXXVIII. The product is subsequently purified over Sephadex G25 [solvent: H₂O/MeOH (85:15, v/v)].

TLC: silica gel; isoPrOH/NH₄OH/H₂O (65:9:15, v/v), Rf≈0.27; cellulose: EtOH/AcONH₄(M) (4:1, v/v), Rf≈0.51.

EXAMPLE LXI

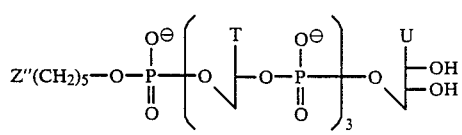

The totally protected nucleotide (1 equivalent) (Example XXXI) is treated with a 2% strength solution of benzene sulfonic acid in CH₂Cl₂/MeOH/H₂O (7:2.5:0.5, v/v) at 10° C. for 50 minutes. The mixture is diluted with chloroform, washed with an aqueous solution of NH₄HCO₃ and dried and concentrated in vacuo. The residue obtained is treated with a molar solution of

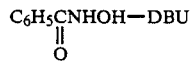

in pyridine (30 equivalents) (2 days at the ambient temperature) and with sodium hydroxide (concentration of sodium hydroxide in the solution ≈0.1N) (45 minutes at the ambient temperature). After neutralization of the reaction mixture with DOWEX 50 (pyridinium form) and evaporation of the solvent, the product is purified over DEAE Sephacel using an elution gradient ($10^{-3}$M–0.5M) of NH₄HCO₃ in H₂0/MeOH (70:30, v/v).

TLC: silica gel; isoPrOH/NH₄OH/H₂O (65:9:15, v/v), Rf≈0.38.

EXAMPLE LXII

| Example | Protected nucleotides | De-protected nucleotides | TLC Cellulose Solvent | Rf |
|---|---|---|---|---|
| LXV | (DMTr)d(bzA∓)₅(CH₂)₅Z″ | d [A—A—A—A—A—(CH₂)₅Z″] | EtOH, AcONH₄(M) (2:6, v/v) | 0.21 |
| LXVI | (DMTr)dbzA ∓ T ∓ bzA ∓ bzA ∓ bzA ∓ T ∓ T ∓ T ∓ anC ∓ bzA ∓ anC ∓ (CH₂)₅Z″ | d [A—T—A—A—A—T—T—C—A—C—(CH₂)₅Z″] | EtOH, AcONH₄(M) (2:6, v/v) | 0.08 |
| LXVII | (DMTr)dbzA ∓ bzA ∓ T ∓ ibG ∓ ibG ∓ T ∓ bzA ∓ bzA ∓ bzA ∓ bzA ∓ T ∓ (CH₂)₅Z″ | d [A—A—T—G—G—T—A—A—A—A—T—(CH₂)₅Z″] | EtOH, AcONH₄(M) (2:6, v/v) | 0.07 |

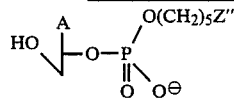

20

The nucleotide (DMTr)d∓bzA∓(CH₂)₅Z″ (1 equivalent) is treated with a molar solutin of

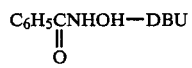

25 in pyridine (10 equivalents) at the ambient temperature overnight. 2 volumes of a molar solution of sodium hydroxide in MeOH/H₂O (2:1, v/v) are added to this solution and stirring is continued at the ambient temperature for 1 day. After the reaction mixture has been neutralized with an anionic resin (pyridinium form), the solvent is driven off in vacuo and the residue is treated with 80% strength acetic acid. The product is then purified over silica gel (preparative plate), solvent; CH₂Cl₂/MeOH (50:50, v/v).

TLC: silica gel; CH₂Cl₂/MeOH (50:50, v/v), Rf≃0.33.

EXAMPLES LXIII and LXIV

De-protection of the compounds XXXIII and XXXIV is carried out as in Example LXII and the products are purified by chromatography on a plate.

| | |
|---|---|
| HO—C—O(CH₂)₅Z″ O—P\\O⊖ | Silica gel; CH₂Cl₂/MeOH (50:50, v/v) TLC: silica gel; CH₂Cl₂/MeOH (50:50, v/v), Rf ≃ 0.43 |
| HO—G—O(CH₂)₅Z″ O—P\\O⊖ | Silica gel; EtOH/AcONH₄(M) (8:2, v/v). |

EXAMPLES LXV to LXVII

The oligonucleotides (XXXV, XXXVI, XXXVII) are de-protected as in Example LXII using 10 equivalents of

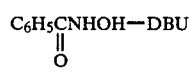

65 per equivalent of arylated phosphoester to be de-protected; the products are subsequently purified over DEAE Sephacel using an elution gradient of NH₄HCO₃ in H₂O/MeOH (70:30, v/v) (10⁻³M to 0.7M for LXV, 0.1M to 0.9M for LXVI and 0.1M to 1M for LXVII).

EXAMPLE LXVIII $$H \left( O \underset{T}{\diagdown} -O-\underset{\underset{O}{\|}}{\overset{Me}{\underset{|}{P}}}-O \underset{T}{\diagdown} -O-\underset{\underset{O}{\|}}{\overset{O^{\ominus}}{P}} \right)_2 -O-(CH_2)_5Z''$$

(1)

$$(DMTr) \left( O \underset{T}{\diagdown} -O-\underset{\underset{O}{\|}}{\overset{Me}{\underset{|}{P}}}-O \underset{T}{\diagdown} -O-\underset{\underset{O}{\|}}{\overset{Ar}{\underset{|}{P}}} \right)_2 -O-(CH_2)_5Z''$$

The procedure followed is as in Example VI, the dinucleotide (DMT)T±T±CNEt being replaced by the compound prepared according to Example XV and the 8-(ω-hydroxypropoxy)-psoralene being replaced by 2-methoxy-6-chloro-9-(ω- hydroxypentylamino)-acridine; the protected product is obtained in a yield of 60%.

(2)

The deprotection was carried out as in Examples XXXXI to LVI; the product is subsequently purified by HPLC [Lichrosorb RP-18 column (Merck); solvent: CH₃CN/aqueous 10% strength by weight solution of triethylammonium acetate (pH=5.5)/water 216:79:713, v/v), flow rate 1.2ml/minute], retention time=7 minutes, 40.

EXAMPLES LXIX and LXX

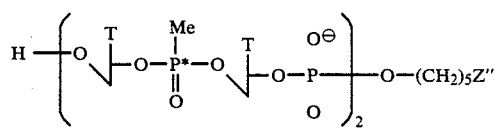

(1)

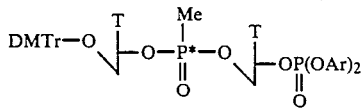

Coupling of the nucleoside 3'-methyl-phosphate XV-1 (1.5 equivalents) with di-(p-chlorophenyl) thymidine 3'-phosphate (1 equivalent) was carried out in the presence of MST (3 equivalents) and the α and β isomers are separated by chromatography over silica TLC: silica gel; $CH_2Cl_2$/MeOH (9:1, v/v)
α isomer: Rf=0.63.
β isomer: Rf=0.58.

(2)

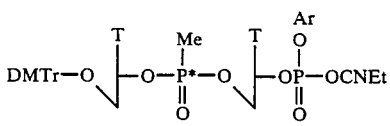

(a) α isomer

The α isomer prepared according to Examples LXIX and LXX-1 is reacted with a solution of pyridine/triethylamine/water (3:1:1, v/v) at 40° C. for 6 hours; the diester formed is then purified by chromatography over silica using the solvent system: $CH_2Cl_2$/MeOH/pyridine (85:15:0.4 v/v). The diester obtained (1 equivalent) is coupled with β-cyanoethanol (2 equivalents) in the presence of MST (3 equivalents); the preparation is subsequently completed as in Example I-2.

α isomer: Rf=0.55 and 0.52 [TLC: silica gel; $CHCl_3$MeOH (9:1, v/v)].

(b) β Isomer

The procedure followed is as above, using the β isomer prepared according to Examples LXIX and LXX-1 as the starting substance, and the β isomer is obtained. β isomer: Rf=0.49 and 0.45 TLC: silica gel; $CHCl_2$MeOH (9:1, v/v).

(3)

The procedure followed is as in Example LXVIII, using each of the α and β isomers of Examples LXIX and LXX-2 as starting substances; the tetranucleotides in the form of, respectively, the α isomer and β isomer are obtained. HPLC [Lichrosorb RP-18 column (Merck); solvent: $CH_3CN$ aqueous 10% stength by weight solution of triethylammonium acetate (pH=5.9)/water (216:79:713, v/v)flow rate 1.2 ml/minute].

LXIX α isomer retention time=7'30"
LXX β isomer retention time=7'46".

EXAMPLES LXXI to LXXVII

The procedure followed is as in Examples XXXV to XXXVII, and the totally protected oligodeoxynucleotides are prepared by coupling blocks according to the equations given below and removing the protective groups as for Examples LXV to LXIII; the deprotected oligonucleotides LXXI to LXXVII are then purified by HPLC.

Example LXXI
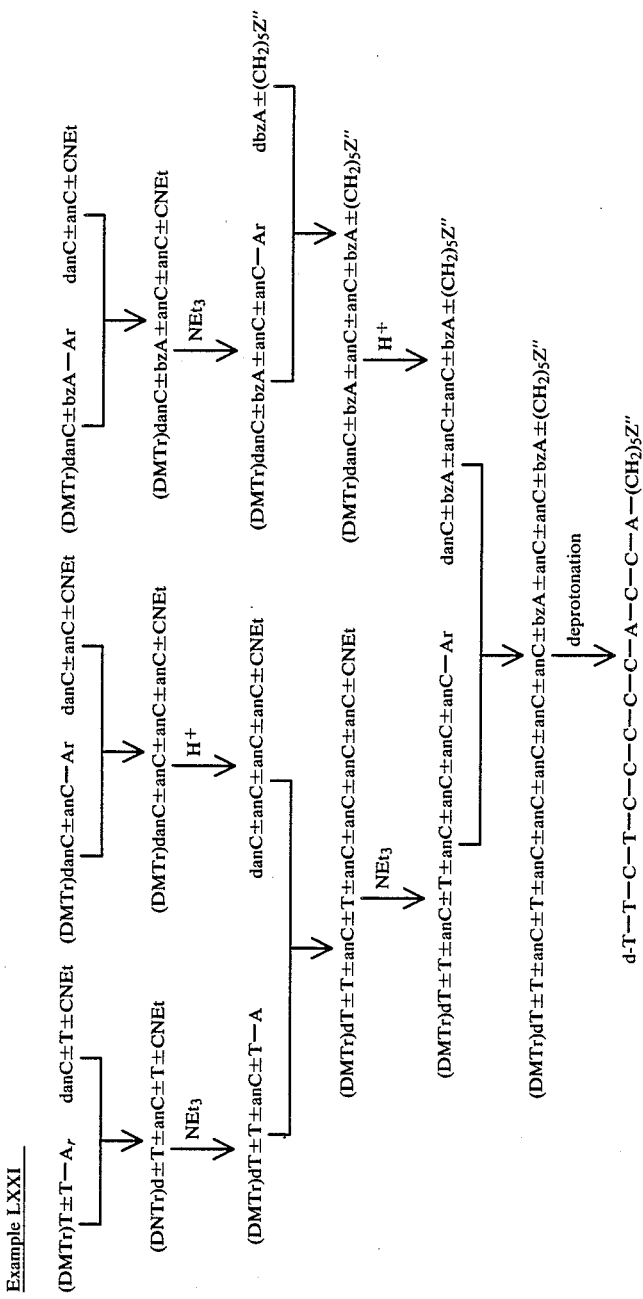

Example LXXII

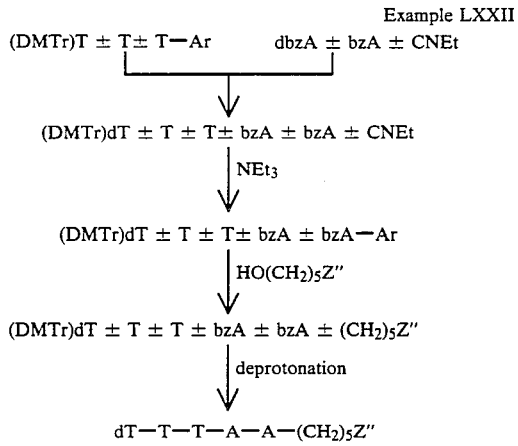

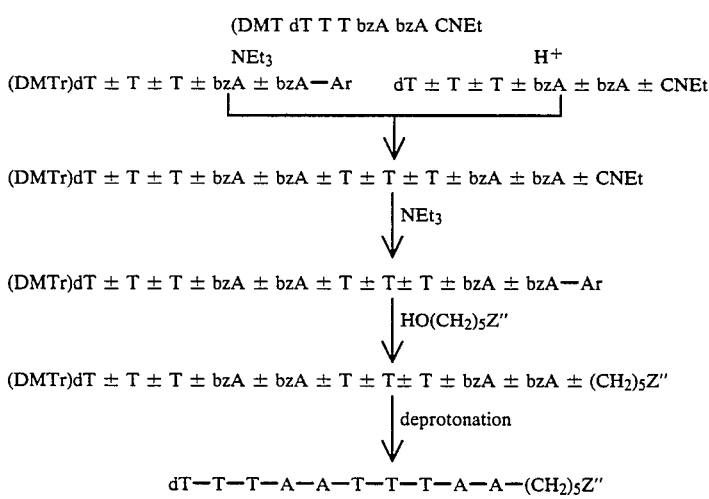

Example LXXIV

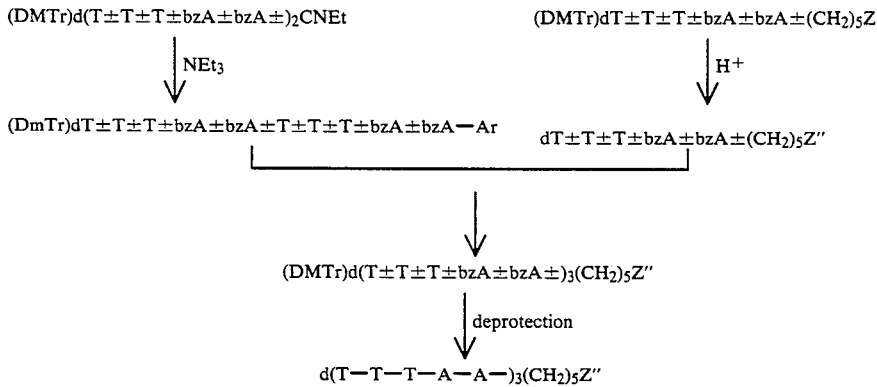

Example LXXV

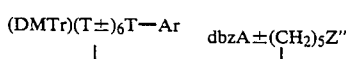

-continued
Example LXXV

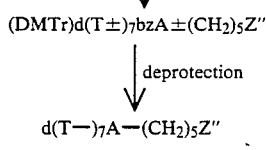

| Examples | System of solvents | Retention time |
|---|---|---|
| LXXI | $A_1$-$B_2$ isocratic with 65% of $B_2$ | 7' 10" |
| LXXII | $B_1$-$B_2$ linear gradient from 35–70% of $B_2$ in 12 minutes, then isocratic | 13' 51" |
| LXXIII | $A'_1$-$B'_2$ isocratic with 60% of $B'_2$ | 3' 35" |

Example LXXIII

| LXXIV | $A'_2$-$B'_2$ isocratic with 25% of $B'_2$ | 7' 55" |
| LXXV | $A'_2$-$B'_2$ isocratic with 45% of $B'_2$ | 5' 30" |

Lichrosorb RP-18 column (Merck); flowrate: 1.2 ml/minute
$A_1$: CH₃CN/TEAc/water (18:88:794, v/v); $A'_1$: CH₃CN/AAc/water (18:88:794, v/v)
$B_1$: CH₃CN/TEAc/water (108:79:713, v/v); $B_2$: CH₃CN/TEAc/water (216:79:713, v/v)
$B'_2$: CH₃CN/AAc/water (216:79:713, v/v)
AAc: aqueous 10% strength by weight solution of ammonium acetate (pH = 5.9)
TEAc: aqueous 10% strength by weight solution of triethylammonium acetate (pH = 5.9)

We claim:
1. An oligonucleotide or an oligodeoxynucleotide consisting of a natural or modified chain of nucleotodes of from 1 to 50 nucleotides or deoxynucleotides to which is attached an intercalating agent via a covalent bond at the 3', 5', or 3' and 5' end or at an internucleotide phosphate of said oligonucleotide or oligodeoxynucleotide, having the formula:

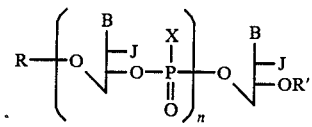

in which
each B, which are identical or different, represents a base of a natural nucleic acid, selected from the group consisting of thymine, adenine, cytosine, guanine or uracil, or 5-bromo-uracil, 8-azido-adenine, and 2, 6-diamino-purine;
each X, which are identical or different, represents
an oxoanion $O^-$,
a thioanion $S^-$,
a $C_1$ to $C_7$ alkyl group,
a $C_1$ to $C_7$ alkoxy group,
a monosubstituted or disubstituted amino in the form of quaternary ammonium salt, wherein the substituent is a $C_1$ to $C_7$ and wherein the amino is linked to the phosphorous by a straight or branched alkyl or alkoxy chain containing 1 to 10 carbon atoms,
a $C_1$-$C_7$ thioalkyl group, or
a —Y—Z group;
each R and R', which are identical or different, [each ] represents a hydrogen atom or a —Y—Z group;
at least one of X, R, or R' is a Y—Z group;
provided that:
when R or R' is a Y—Z group, Y—Z represents

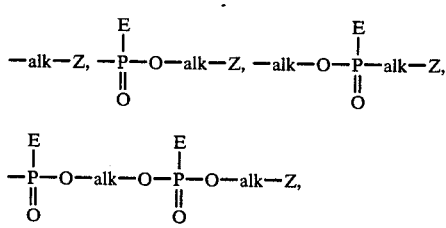

when X is a Y—Z group Y—Z represents —alk—Z, or

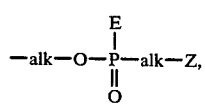

wherein alk is a straight or branched chain alkylene containing 1 to 10 carbon atoms,
each E, which are identical or different, represents
an oxoanion $O^-$,
a thioanion $S^-$,
a $C_1$ to $C_7$ alkyl group,
a $C_1$ to $C_7$ alkoxy group,
a monosubstituted or disubstituted amino in the form of quaternary ammonium salt, wherein the substituent is a $C_1$ to $C_7$ alkyl and wherein the amino is linked to the phosphorous by a straight or branched alkyl or alkoxy chain containing 1 to 10 carbon atoms,
a $C_1$-$C_7$ thioalkyl group;
each J, which are identical or different, represents a hydrogen atom or a hydroxyl group;
each Z, which are identical or different, represents an intercalating agent selected from the group consisting of acridine, furocoumarin,

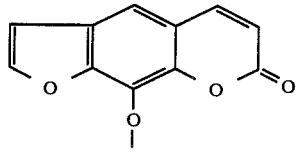

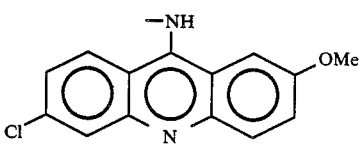

and derivatives thereof; and
n is an integer having a value from 0 to 50.

2. The oligonucleotide or oligodeoxynucleotide according to claim 1, wherein B is selected from the group consisting of thymine, adenine, cytosine, guanine, uracil, 5-bromo-uracil, or 8-azido-adenine.

3. An oligonucleotide or an oligodeoxynucleotide according to claim 1, wherein said oligonucleotide or oligodeoxynucleotide comprising a chain of natural or modified nucleotides or dedeoxynucleotides to which an intercalating group is attached via a covalent bond having the formula:

$(T-)_n(Y_1)Z_1$;

$Z_2(Y_2)(-T)_n$;

$Z_2(Y_2)(-T)_n(Y_1) Z$

T— and —T are a thymidine linked through a phosphodiester bond,
n is an integer from 1 to 50,
$Y_1$ and $Y_2$ are selected from a $C-_1$ to $C-_7$ alkylene or a

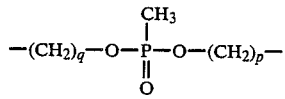

wherein p and q are whole numbers from 1 to 10, and
$Z_1$ and $Z_2$, which are identical or different, each represents an intercalating agent selected from the group consisting of acridine, furocoumarin,

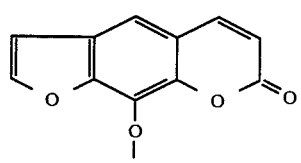

-continued

[structure: 9-amino-6-chloro-2-methoxyacridine]

and derivatives of said intercalating agents.

4. An oligonucleotide or an oligodeoxynucleotide comprising a chain of natural or modified nucleotides or deoxynucleotides to which an intercalating group is attached via a covalent bond having the formula:

(A—)$_n$(CH$_2$)$_n$Z;

(G—)$_n$(CH$_2$)$_n$Z;

(C—)$_n$(CH$_2$)$_n$Z, whe

A— is adenosine linked through a phosphodiester bond,
C— is cytidine linked through a phosphodiester bond,
G— is guanosine linked through a phosphodiester bond,
n is an integer from 1 to 25,
Z represents an intercalating agent selected from acridine, furocoumarin,

[structure: furocoumarin]

[structure: 9-amino-6-chloro-2-methoxyacridine]

and derivatives of said intercalating agents.

5. An oligonucleotide or an oligodeoxynucleotide comprising a natural or modified chain of nucleotides or deoxynucleotides to which an intercalating group is attached via a covalent bond having the sequence selected from the group consisting of:

d
(A—T—A—A—A—T—T—C—A—C—(CH$_2$)$_n$Z, d
(A—A—T—G—G—T—A—A—A—A—T—(CH$_2$)$_n$Z), d
(T—T—C—T—C—C—C—C—C—A—C—C—A—(CH$_2$)$_n$Z), d (T—T—T—A—A—(CH$_2$)$_n$Z), d
(T—T—T—A—A—T—T—T—A—A—(CH$_2$)$_n$Z), d
(T—T—T—A—A—T—T—T—A—A—T—T—T—A—A—(CH$_2$)$_n$Z), and d (T—T—T—T—T—T—T—A—(CH$_2$)$_n$Z), wherein:
T— is thymidine linked through a phosphodiester bond,
A— is adenosine linked through a phosphodiester bond,
C— is cytidine linked through a phosphodiester bond,
G— is guanidine linked through a phosphodiester bond,
n is an integer from 1 to 25, and
Z represents an intercalating agent selected from acridine, furocoumarin,

[structure: furocoumarin]

[structure: 9-amino-6-chloro-2-methoxyacridine]

and derivatives of said intercalating agents.

6. An oligonucleotide or oligodeoxynucleotide comprising a chain of natural or modified nucleotides or deoxynucleotides to which an intercalating group is attached via a covalent bond having the formula:

Z'(CH$_2$)$_3$∓T∓T∓T∓T∓T∓(CH$_2$)$_3$Z'

Z"(CH$_2$)$_5$∓T∓T∓T∓T∓T∓(CH$_2$)$_5$Z"

Z'(CH$_2$)$_3$—T—T—T—T—(CH$_2$)$_3$Z'

Z"(CH$_2$)$_5$—T—T—T—T—(CH$_2$)$_5$Z"

Z"(CH$_2$)$_5$—(T—)$_8$(CH$_2$)$_5$Z"

T—(CH$_2$)$_3$Z'

T—(CH$_2$)$_3$Z"

T—(CH$_2$)$_5$Z"

T—T—T—(CH$_2$)$_5$Z"

T—T—T—T—(CH$_2$)$_3$Z'

T—T—T—T—(CH$_2$)$_5$Z"

[structure showing Z"H with phosphate-linked thymidine repeats ending in O(CH$_2$)$_5$Z"]

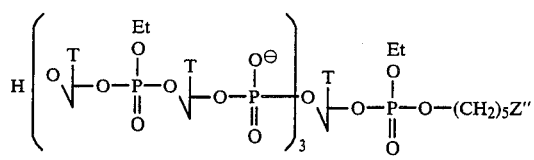

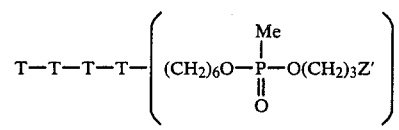

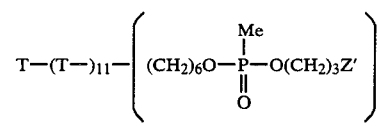

(T—)₄(CH₂)₄Z″

(T—)₈(CH₂)₅Z″

(T—)₈(CH₂)₆Z″

(T—)₁₂(CH₂)₅Z″

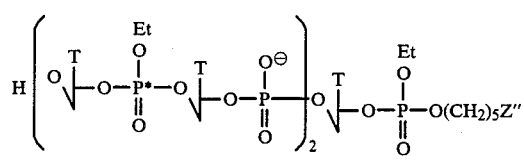

Z″(CH₂)₅(—T)₇—T

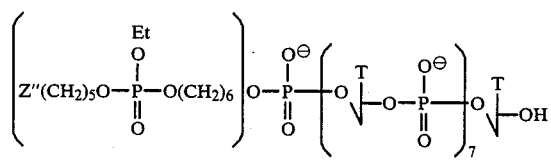

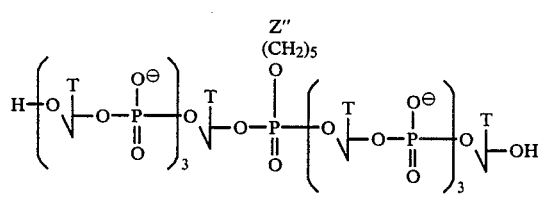

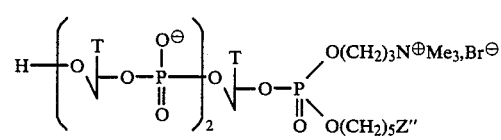

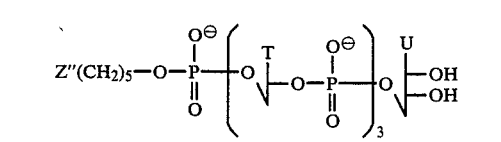

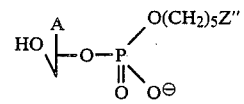

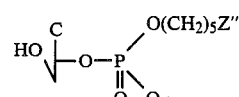

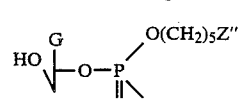

d(A—A—A—A—A—(CH₂)₅Z″)

d(A—T—A—A—A—T—T—C—A—C—(CH₂)₅Z″)

d(A—A—T—G—G—T—A—A—A—A—T—(CH₂)₅Z″)

wherein
T is thymine
T— and —T are thymidine linked through a phosphodiester bond,
A is adenine,
C is cytosine,
G is guanine,
U is uracil,
∓T and T∓ represent thymidine linked through a a phosphotriester bond wherein each phosphate is protected by a p-chlorophenyl group,
A— is adenosine linked through a phosphodiester bond,
C— is cytidine linked through a phosphodiester bond,
G— is guanosine linked through a phosphodiester bond,
Z′ is

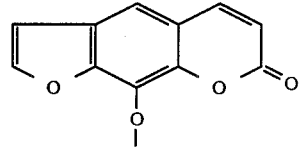

and
Z″ is

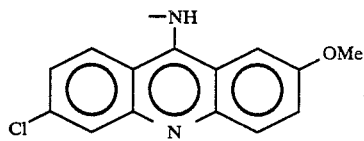

7. The oligonucleotide or oligodeoxynucleotide according to claim 6, wherein said oligonucleotide or oligodeoxynucleotide is in the form of an optically pure R or S isomer or a mixture thereof.

* * * * *

UNITED STATES PATENT AND TRADEMARK OFFICE
CERTIFICATE OF CORRECTION

PATENT NO. : 4,835,263

DATED : May 30, 1989

INVENTOR(S) : Thanh Nguyen et al.

It is certified that error appears in the above-identified patent and that said Letters Patent is hereby corrected as shown below:

Column 49, line 3, delete "nucleotodes" and insert -- nucleotides --.

Column 49, line 28, after "$C_7$" but before "and" insert -- alkyl --.

Column 49, lines 34-35, delete "[each]".

Column 50, line 43, after "$Z_2(Y_2)(-T)_n(Y_1)Z$" but above line 44 insert -- wherein: --.

Column 51, line 20, delete "whe" and insert -- wherein: --.

Column 51, line 53, delete the "d".

Column 51, line 54, insert -- d -- at the beginning of the line directly before the parenthetical.

Column 51, line 55, after "Z" delete the "," and insert -- ), --.

Column 51, line 57, delete the "d".

Column 51, line 58, insert -- d -- at the beginning of the line directly before the parenthetical.

Column 51, line 60, delete the "d".

UNITED STATES PATENT AND TRADEMARK OFFICE
CERTIFICATE OF CORRECTION

PATENT NO. : 4,835,263

DATED : May 30, 1989

INVENTOR(S) : Thanh Nguyen et al.

It is certified that error appears in the above-identified patent and that said Letters Patent is hereby corrected as shown below:

Column 51, line 61, insert -- d -- at the beginning of the line directly before the parenthetical.

Column 51, line 66, delete the "d".

Column 51, line 67, insert -- d -- at the beginning of the line directly before the parenthetical.

Column 54, line 30, delete the indefinite article "a", first occurrence.

Column 54, line 57, a -- . -- should be inserted after the chemical formula represented.

Signed and Sealed this

Twentieth Day of March, 1990

Attest:

JEFFREY M. SAMUELS

Attesting Officer

Acting Commissioner of Patents and Trademarks